US011096920B2

(12) United States Patent
Schioppi et al.

(10) Patent No.: US 11,096,920 B2
(45) Date of Patent: *Aug. 24, 2021

(54) LOW-DOSE DOXEPIN FORMULATIONS AND METHODS OF MAKING AND USING THE SAME

(71) Applicant: Currax Pharmaceuticals LLC, Morristown, NJ (US)

(72) Inventors: Luigi Schioppi, Escondido, CA (US); Brian Talmadge Dorsey, Encinitas, CA (US); Michael Skinner, San Diego, CA (US); John Carter, Keswick (CA); Robert Mansbach, San Diego, CA (US); Philip Jochelson, San Diego, CA (US); Roberta L. Rogowski, Rancho Santa Fe, CA (US); Cara Baron Casseday, San Diego, CA (US); Meredith Perry, El Cajon, CA (US); Bryan Knox, San Diego, CA (US)

(73) Assignee: Currax Pharmaceuticals LLC, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/779,901

(22) Filed: Feb. 3, 2020

(65) Prior Publication Data

US 2020/0170991 A1     Jun. 4, 2020

Related U.S. Application Data

(63) Continuation of application No. 15/911,496, filed on Mar. 5, 2018, now Pat. No. 10,548,871, which is a continuation of application No. 15/394,912, filed on Dec. 30, 2016, now Pat. No. 9,907,780, which is a continuation of application No. 13/898,364, filed on May 20, 2013, now Pat. No. 9,532,971, which is a continuation of application No. 12/101,917, filed on Apr. 11, 2008, now abandoned.

(60) Provisional application No. 60/911,806, filed on Apr. 13, 2007.

(51) Int. Cl.
*A61K 31/335* (2006.01)
*A61K 9/20* (2006.01)
*A61K 9/28* (2006.01)
*A61K 47/02* (2006.01)
*A61K 47/38* (2006.01)

(52) U.S. Cl.
CPC .......... *A61K 31/335* (2013.01); *A61K 9/2009* (2013.01); *A61K 9/2054* (2013.01); *A61K 9/2806* (2013.01); *A61K 47/02* (2013.01); *A61K 47/38* (2013.01)

(58) Field of Classification Search
CPC ...... A61K 31/335; A61K 47/02; A61K 47/38; A61K 9/2009; A61K 9/2054; A61K 9/2806; A61P 25/20
See application file for complete search history.

(56) References Cited

U.S. PATENT DOCUMENTS

| | | |
|---|---|---|
| 3,420,851 A | 1/1969 | Bloom et al. |
| 3,438,981 A | 4/1969 | Stach |
| 3,509,175 A | 4/1970 | Tretter |
| 4,110,438 A | 8/1978 | Gahwyler |
| 4,434,171 A | 2/1984 | Müller |
| 4,517,179 A | 5/1985 | Raghunathan |
| 4,833,154 A | 5/1989 | Jean-Louis et al. |
| 5,030,632 A | 7/1991 | Sterling |
| 5,116,852 A | 5/1992 | Gammans |
| 5,332,661 A | 7/1994 | Adamczyk et al. |
| 5,502,047 A | 3/1996 | Kavey |
| 5,585,115 A | 12/1996 | Sherwood et al. |
| 5,643,897 A | 7/1997 | Kavey |
| 5,722,578 A | 3/1998 | Van Erden et al. |
| 5,725,883 A | 3/1998 | Staniforth et al. |
| 5,741,524 A | 4/1998 | Staniforth et al. |
| 5,858,412 A | 1/1999 | Staniforth et al. |
| 5,866,166 A | 2/1999 | Staniforth et al. |
| 5,948,438 A | 9/1999 | Staniforth et al. |
| 5,965,166 A | 10/1999 | Hunter et al. |
| 6,103,219 A | 8/2000 | Sherwood et al. |
| 6,106,865 A | 8/2000 | Staniforth et al. |
| 6,211,229 B1 | 4/2001 | Kavey |
| 6,217,907 B1 | 4/2001 | Hunter et al. |
| 6,217,909 B1 | 4/2001 | Sherwood et al. |
| 6,219,674 B1 | 4/2001 | Classen |
| 6,344,487 B1 | 2/2002 | Kavey |
| 6,358,533 B2 | 3/2002 | Sherwood et al. |
| 6,391,337 B2 | 5/2002 | Hunter et al. |
| 6,395,303 B1 | 5/2002 | Staniforth et al. |
| 6,403,597 B1 | 6/2002 | Wilson et al. |

(Continued)

FOREIGN PATENT DOCUMENTS

| | | |
|---|---|---|
| WO | 1999/040898 A2 | 8/1999 |
| WO | 2000/010554 A2 | 3/2000 |

(Continued)

OTHER PUBLICATIONS

ABPI (Association of the British Pharmaceutical Industry) Compendium of Data Sheets and Summaries of Product Characteristics, 1996-1997; Pfizer Limited, p. 751-752.

(Continued)

*Primary Examiner* — Matthew P Coughlin
*Assistant Examiner* — Thurman Wheeler
(74) *Attorney, Agent, or Firm* — Servilla Whitney LLC

(57) ABSTRACT

The invention disclosed herein generally relates to low-dose oral doxepin pharmaceutical formulations and the use of these formulations to promote sleep.

20 Claims, 21 Drawing Sheets

(56) References Cited

U.S. PATENT DOCUMENTS

| | | | |
|---|---|---|---|
| 6,407,128 | B1 | 6/2002 | Scaife et al. |
| 6,471,994 | B1 | 10/2002 | Staniforth et al. |
| 6,521,261 | B2 | 2/2003 | Sherwood et al. |
| 6,584,472 | B2 | 6/2003 | Classen |
| 6,683,102 | B2 | 1/2004 | Scaife et al. |
| 6,746,693 | B2 | 6/2004 | Staniforth et al. |
| 6,852,336 | B2 | 2/2005 | Hunter et al. |
| 6,858,231 | B2 | 2/2005 | Sherwood et al. |
| 6,866,867 | B2 | 3/2005 | Staniforth et al. |
| 6,936,277 | B2 | 8/2005 | Staniforth et al. |
| 7,135,196 | B2 | 11/2006 | Stockham |
| 7,179,488 | B2 | 2/2007 | Sherwood et al. |
| 7,276,536 | B2 | 10/2007 | Urata et al. |
| 7,452,872 | B2 | 11/2008 | Johnson |
| 7,915,307 | B2 | 3/2011 | Casseday et al. |
| 8,097,625 | B2 | 1/2012 | Lalji et al. |
| 2002/0037828 | A1 | 3/2002 | Wilson et al. |
| 2002/0197235 | A1 | 12/2002 | Moran |
| 2003/0175355 | A1 | 9/2003 | Tobyn et al. |
| 2003/0206978 | A1 | 11/2003 | Sherwood et al. |
| 2003/0235617 | A1 | 12/2003 | Martino et al. |
| 2004/0063721 | A1 | 4/2004 | Deecher et al. |
| 2004/0115142 | A1 | 6/2004 | Sherwood et al. |
| 2004/0224017 | A1 | 11/2004 | Mulye |
| 2004/0265374 | A1 | 12/2004 | Staniforth et al. |
| 2004/0265375 | A1 | 12/2004 | Platteeuw et al. |
| 2005/0013861 | A1 | 1/2005 | Sherwood et al. |
| 2005/0118261 | A1 | 6/2005 | Oien et al. |
| 2005/0123609 | A1 | 6/2005 | Hirsh et al. |
| 2005/0147673 | A1 | 7/2005 | Staniforth et al. |
| 2005/0171160 | A1 | 8/2005 | Edgar et al. |
| 2005/0196439 | A1 | 9/2005 | Sherwood et al. |
| 2005/0214365 | A1 | 9/2005 | Yousef et al. |
| 2005/0239838 | A1 | 10/2005 | Edgar et al. |
| 2005/0256165 | A1 | 11/2005 | Edgar et al. |
| 2006/0008522 | A1 | 1/2006 | Staniforth et al. |
| 2006/0228487 | A1 | 10/2006 | Schaible et al. |
| 2007/0281990 | A1 | 12/2007 | Rogowski et al. |
| 2008/0058407 | A1 | 3/2008 | Baron et al. |
| 2008/0058408 | A1 | 3/2008 | Rogowski et al. |
| 2008/0182890 | A1 | 7/2008 | Jochelson et al. |
| 2009/0042971 | A1 | 2/2009 | Rogowski et al. |
| 2009/0042972 | A1 | 2/2009 | Rogowski et al. |
| 2009/0074862 | A1 | 3/2009 | Schioppi et al. |
| 2010/0105614 | A1 | 4/2010 | Jochelson |
| 2010/0179214 | A1 | 7/2010 | Dubé et al. |
| 2010/0179215 | A1 | 7/2010 | Dubé et al. |
| 2010/0227916 | A1 | 9/2010 | Kavey et al. |
| 2011/0077200 | A1 | 3/2011 | Jochelson et al. |
| 2011/0166215 | A1 | 7/2011 | Casseday et al. |
| 2011/0178166 | A1 | 7/2011 | Rogowski et al. |
| 2011/0318412 | A1 | 12/2011 | Schioppi et al. |
| 2012/0088822 | A1 | 4/2012 | Rogowski et al. |
| 2012/0245222 | A1 | 9/2012 | Rogowski et al. |
| 2013/0096188 | A1 | 4/2013 | Dube et al. |
| 2013/0102658 | A1 | 4/2013 | Dube et al. |

FOREIGN PATENT DOCUMENTS

| | | |
|---|---|---|
| WO | 2000050025 A1 | 8/2000 |
| WO | 2003004009 A1 | 1/2003 |
| WO | 2007047519 A2 | 6/2003 |
| WO | 2003066029 A2 | 8/2003 |
| WO | 2007136845 A2 | 11/2007 |
| WO | 2007142810 A2 | 12/2007 |
| WO | 2007142811 A2 | 12/2007 |

OTHER PUBLICATIONS

ABPI (Association of the British Pharmaceutical Indusry) Data Sheet Compendium 1991-1992; Pfizer Limited, p. 1147-1149.
ABPI (Association of the British Pharmaceutical Industry) Data Sheet Compendium 1993-1994; Pfizer Limited, p. 1205-1207.
ABPI (Association of the British Pharmaceutical Industry) Data Sheet Compendium 1994-1995; Pfizer Limited, p. 1150-1151.
ABPI (Association of the British Pharmaceutical Industry) Data Sheet Compendium 1995-1996; Pfizer Limited, p. 1239-1240.
ABPI (Association of the British Pharmaceutical Industry) Data Sheet Compendium 1998-1999; Pfizer Limited, p. 970-971.
ABPI (Association of the British Pharmaceutical Industry) Medicines Compendium, 2002; Pfizer Limted, p. 1792-1793.
Adapin, Drug Side Effects, http://www.depression-guide.com/adapin.htm, 2005, 1-3.
Albemarle Pulmonary Medicine Associates, http://apmanc.com/PatientEducation/INSOMNIA.HTM, 2000, pp. 1-4.
Ambien (Zolpidem Tartrate) tablets CIV. Highlights of Prescribing Information. Revised Jun. 2009. Sanofi-Aventis U.S. LLC. p. 1-8.
Doxal. Laakeopas. Retrieved Nov. 28, 2005 from <http://www.coronaria.fi/www/mtv3/laakkeet.php?id=299>.
Doxal. Laakkeet. Retrieved Nov. 28, 2005 from <http://www.tohori.fi/aakkeet/uote.php3?1D=412>.
Doxepin. Find Treatment & Support. The most reliable cancer treatment information. Cancer.org. Web download: Jul. 6, 2010. <http:www.cancer.org/docroot/CDG/content/CDG doxepin.asp?internal=1>p. 1-6.
German Federal Gazette (BAnz) No. 240 of Dec. 22, 1992, p. 9545 (vol. 44).
Guidance for Industry SUPAC-IR/MR: Immediate Release and Modified Release Solid Oral Dosage Forms—Manufacturing Equipment Addendum, Jan. 1999.
Lunesta (Eszopiclone) Tablets 1 mg, 2 mg, 3 mg. Prescribing Information. Package Insert. Sepracor Inc. Jan. 2009. p. 1-2.
National Academy of Sciences, Sleeping Pills, Insomnia, and Medical Practice, Institute of Medicine, 32-33, 103, 125, 149, 169, 198, (1979).
Natrol Melantonin 3 mg. 60 Tablets. Dietary Supplement. Manufactured by Natrol, Inc. Label. p. 1-3.
New Drug Application 16-798 for Sinequan approved in 1978 (includes evaluation of insomnia indication on pp. 46-47, 54, 57, 59.
NyQuil Cold & Flu. Nightime Relief. Acetaminophe, Doxylamine, Dextromethorphan, Alcohyl 10%. 6 Fl. Oz. Vicks Label. 2 pages.
NyQuil Oral. Drugs & Medications. WebMD. Web download: Jul. 6, 2010. http://www.webmed.com/drugs-6104-NyQuil+ Oral.aspx?drugid=6104&drugname=NyQuil+ Oral&source=1, p. 1-3.
Nytol Oral. Drugs & Medications—WebMD. Web download: Jul. 6, 2010. http://www. webmd. com/d rugs/d rug-10538-Nytol+Oral.aspx?drugid=10538&drugname=Nytol+Oral&source=O. p. 1-2.
Nytol Quickcaps with Dephenhydramine HCI. Nightime Sleep-Aid. 72 Caplets. Label. 4 pages.
Seminar on Psychosomatics, Auspices of Academy of Psychosomatic Medicine, p. 4-63 (1968).
Somazon Pharmaceuticals Announces Acceptance for Filing of New Drug Application for Silencor™ for the Treatment of Insomnia, Somaxon Pharmaceuticals Press Release, San Diego, CA, p. 1-5 (Apr. 15, 2008).
Somaxon Pharmaceuticals Announces Completion of 26-Week Transgenic Mouse Carcinogenicity Study of Silencor™ , Somaxon Pharmaceuticals Press Release, San Diego, CA, p. 1-3 (Jan. 9, 2008).
Somaxon Pharmaceuticals Announces Data to be Presented at American Psychiatric Association 161st Annual Meeting, Somaxon Pharmaceuticals Press Release, San Diego, CA (May 2, 2008).
Somaxon Pharmaceuticals Announces Data to be Presented at American Psychiatric Association 161st Annual Meeting, Somaxon Pharmaceuticals Press Release, San Diego, CA, p. 1-7 (May 7, 2008).
Somaxon Pharmaceuticals Announces FDA Approval of Silenor® (Doxepin) for the Treatment of Insomnia, Somaxon Pharmaceuticals Press Release, San Diego, CA, p. 1-5 (Mar. 18, 2010).
Somaxon Pharmaceuticals Announces Positive Phase 3 Results with Silenor™ for the Treatment of Adults with Chronic Insomnia, Somaxon Pharmaceuticals, p. 1-5, (Apr. 10, 2006).
Somaxon Pharmaceuticals Announces Positive Results in a Phase II Dose-Finding Study of Low-dose Doxepin in Adults with Primary Sleep Maintenance Insomnia, Somaxon Pharmaceuticals, p. 1-2 (Jan. 6, 2005).

(56) References Cited

OTHER PUBLICATIONS

Somaxon Pharmaceuticals Announces Positive Results in a Phase II Dose-Finding Study of Low-Dose Doxepin in Elderly Patients with Primary Sleep Maintenance Insomnia, Somaxon Pharmaceuticals, p. 1-3, (Apr. 21, 2005).

Somaxon Pharmaceuticals Announces Presentation of Phase II Silenor® Data at the Associated Professional Sleep Societies Annual Meeting, Somaxon Pharmaceuticals, p. 1-2, (Jun. 20, 2006).

Somaxon Pharmaceuticals Announces the Completion of Enrollment in a Phase II Study Evaluation S0-101 for the Treatment of Sleep Maintenance Insomnia in Adults, Somaxon Pharmaceuticals, p. 1, (Oct. 7, 2004).

Somaxon Pharmaceuticals Presents Analyses of Silenor Clinical Data at the American Psychiatric Association Annual Meeting, Somaxon Pharmaceuticals Press Release, San Diego, CA, p. 1-6 (May 20, 2009).

Somaxon Pharmaceuticals Presents Pharmacological Data on Doxepin at the 21st European College of Neuropsychopharmacolgy Congress, Somaxon Pharmaceuticals Press Release, San Diego, CA, p. 1-3 (Sep. 2, 2008).

Somaxon Pharmaceuticals Provides Update on New Drug Application for Silenor® (Doxepin) for the Treatment of Insomnia, Somaxon Pharmaceuticals Press Release, San Diego, CA, p. 1-4 (Apr. 7, 2009).

Somaxon Pharmaceuticals Provides Update on New Drug Application for Silenor® for the Treatment of Insomnia, Somaxon Pharmaceuticals Press Release, San Diego, CA, p. 1-3 (Jan. 21, 2010).

Somaxon Pharmaceuticals Provides Update on Preclinical and Clinical Programs for Silenor™, Somaxon Pharmaceuticals Press Release, San Diego, CA, p. 1-2 (Sep. 11, 2006).

Somaxon Pharmaceuticals Provides Update on Silenor® Development Program for the Treatment of Insomnia, Somaxon Pharmaeuticals, p. 1-5 (Jul. 19, 2006).

Somaxon Pharmaceuticals Provides Update on Silenor™ Development Program, Somaxon Pharmaceuticals Press Release, San Diego, CA, p. 1-3 (May 9, 2007).

Somaxon Pharmaceuticals Provides Update of Silenor™ Preclinical Program, Somaxon Pharmaceuticals Press Release, San Diego, CA, p. 1-7 (Feb. 13, 2007).

Somaxon Pharmaceuticals Receives Complete Response Letter from FDA for Silenor®(Doxepin), Somaxon Pharmaceuticals Press Release, San Diego, CA, p. 1-3 (Feb. 26, 2009).

Somaxon Pharmaceuticals Receives Complete Response Letter form the FDA FOR Silenor® NOA, Somaxon Pharmaceuticals Press Release, San Diego, CA, p. 1-3 (Dec. 7, 2009).

Sonata Official FDA information, side effects and uses. Drug Information Online. Drugs.com. Web. Jul. 6, 2010. http://www.drugs.com/pro/sonata.html. pp. 1-22.

Tylenol PM Oral. Drugs & Medications—WebMD. Web download: Jul. 6, 2010. http://www.webmd.com/drugs/drug-74986—Tylenol+PM+Oral.aspx?drugid=74986&drugname=Tylenol+PM+Oral&source=1. pp. 1-3.

Final Office Action in U.S. Appl. No. 14/804,595 dated Mar. 21, 2016, 10 pages.

Final Office Action in U.S. Appl. No. 13/692,415 dated Feb. 19, 2016, 15 pages.

Final Office Action in U.S. Appl. No. 13/692,715 dated Mar. 23, 2016, 19 pages.

| FIG. 3-1 | FIG. 3-2 | FIG. 3-3 |
|---|---|---|

*FIG. 3*

LOW-DOSE DOXEPIN FORMULATIONS AND METHODS OF MAKING AND USING THE SAME

INCORPORATION BY REFERENCE TO RELATED APPLICATIONS

Any and all priority claims identified in the Application Data Sheet, or any correction thereto, are hereby incorporated by reference under 37 CFR 1.57.

FIELD

Embodiments of the invention disclosed herein relate to low-dose oral doxepin pharmaceutical formulations, methods of making the formulations, and the use of these formulations to promote sleep.

BACKGROUND

Low doses of doxepin can be used to treat sleep disorders, such as insomnia. Sleep is essential for health and quality of life. Insomnia is a growing health problem in the United States. It is believed that more than 10-15 million people suffer from chronic insomnia and up to an additional 70 million people suffer from some form of insomnia each year. Insomnia is a condition characterized by difficulty falling asleep (sleep onset), waking frequently during the night (fragmented sleep), waking too early (premature final awakening), and/or waking up feeling un-refreshed. In the National Sleep Foundation's (NSF) Sleep in America Poll 2005, 42% of survey respondents reported that they awoke frequently during the night, 22% of adults reported waking too early and not being able to return to sleep and 38% reported waking and feeling un-refreshed.

Doxepin is a tricyclic compound currently approved for treatment of depression or anxiety at a daily dose of 75 mg to 300 mg. Non-liquid forms of doxepin are currently available in 10, 25, 50, 75, 100 and 150 mg capsules. Liquid concentrate doxepin is available in a dosage of 10 mg/mL. It should be noted that some embodiments can specifically exclude formulations of doxepin in capsule form, in particular capsules with a powder therein. Capsules with 10 or more mg of doxepin can be excluded from some embodiments. Also, gelatin coated capsules with or without a powder therein can be excluded from some embodiments. Methods of treating sleep using 10 mg capsules or drug taken (e.g., taking a fraction of the powder from the capsule) or derived (e.g., diluting material from a capsule prior to taking) from 10 mg capsules can be specifically excluded from some embodiments.

Making low dose formulations can present technical and economic challenges that are not present for higher dose formulations. Furthermore, existing doxepin formulations do not take into account the unique aspects of sleep disorders.

Embodiments of the invention provide low dose formulations of doxepin and doxepin compounds, and also address and overcome the challenges and problems associated with formulating and manufacturing low-dose doxepin dosage forms.

SUMMARY

Embodiments of the invention disclosed herein relate to low dose doxepin formulations. Also, some embodiments relate to manufacturing processes for the formulations, as well as methods of using the formulations. In some aspects the formulations have one or more desirable physical properties, have preferable functional characteristics, and/or permit efficient and economical manufacturing of low dose doxepin dosage forms.

In the development of pharmaceutical dosage forms, it can be desirable to achieve any of several different objectives. For example, preferably the dosage form can be uniform with respect to drug substance content, fast dissolving, stable, easy to swallow, palatable, and otherwise acceptable to patients in order to maximize patient compliance. In certain contexts, early and/or accelerated onset of drug action also can be advantageous. For example, in the context of sleep, early onset of drug action can be important due to the discreet window of time in which a patient needs to sleep. Also in the context of sleep, the dosage form preferably maintains sleep for a full 7 or 8 hour sleep cycle without significant next-day sedation.

Additionally, it may be desirable to have a manufacturing process that is economical, efficient, robust, and preferably, simple-requiring a minimal number of steps and/or excipients. Furthermore, the active ingredient and excipients preferably have suitable flow properties to ensure efficient mixing and acceptable content uniformity, weight uniformity, hardness, and friability of the final dosage form. Good flow properties also may be beneficial for precise volumetric feeding of the material to a die cavity. However, efficient mixing and acceptable content uniformity are difficult to achieve for low dose dosage forms.

Mixed particle sized powders can segregate due to operational vibrations, resulting in final dosage forms with poor drug or active pharmaceutical ingredient (API) content uniformity. Active substances with a small particle size mixed with excipients having a larger particle size will typically segregate or de-mix during the formulation process. The problem of small particle size and poor flowability can be addressed by enlarging the particle size of the active substance, usually by granulation of the active ingredient either alone or in combination with a filler and/or other conventional excipients. Granulation processes may be energy intensive unit operations requiring complicated and expensive equipment as well as technical skill.

Extensive laboratory and full-scale research have resulted in a new and inventive process for directly compressing low-dose doxepin dosage forms. Accordingly, embodiments of the invention disclosed herein address and achieve one or more of the above-mentioned considerations. Some embodiments surprisingly achieve several or many of the considerations.

In particular, embodiments disclosed herein relate to pharmaceutical dosage forms comprising low doses of doxepin hydrochloride, methods of manufacturing low-dose doxepin dosage forms, and methods of using the formulations and dosage forms. Preferably, the low doses of doxepin hydrochloride can be provided as rapidly dissolving dosage forms, as described herein, which can be advantageously used for treatment of insomnia. In some aspects, the formulations have one or more of: improved friability, compression, dissolution, uniformity, dissolvability, palatability, and the like. Also, in some aspects, the formulations can permit at least one or more of: rapid onset, greater and/or more rapid plasma levels, and the like.

Additional embodiments disclosed herein relate to new and economic methods of manufacture for low-dose dosage forms of doxepin, including, for example, on a large scale. In a preferred embodiment, the methods of manufacture can achieve uniformity of drug substance content and overcome segregation issues that can plague low dose formulations, and can do so in an economical and efficient manner. Some embodiments of the invention relate to low dose doxepin formulations that are amenable to direct compression and that produce a high yield of low dose doxepin dosage forms having acceptable content uniformity, hardness, and friability.

Thus, embodiments of the invention disclosed herein relate to pharmaceutical compositions comprising from about 0.5 to about 9 mg of doxepin, or a pharmaceutically acceptable salt or prodrug thereof, and from about 20% to about 99.9% w/w silicified microcrystalline cellulose. In one embodiment, silicified microcrystalline cellulose (SMCC) can be provided in an amount of about 92% to about 99.8% w/w. The compositions can further comprise from about 0.1 to about 1.5% w/w colloidal silicon dioxide. In another embodiment, the compositions further comprise from about 0.25 to about 1.5% w/w magnesium stearate. In another embodiment, doxepin can be provided in an amount of about 0.8 mg to about 2 mg or about 1 to about 2 mg. In yet another embodiment, doxepin is provided in an amount of about 1 mg. SMCC can be provided in an amount of about 98.5% w/w. In one aspect, doxepin is provided in an amount of about 2.5 mg to about 4 mg or about 3 to about 4 mg. In another aspect, doxepin is provided in an amount of about 3 mg. In one embodiment, SMCC is provided in an amount of about 96.7% w/w. In another embodiment, doxepin is provided in an amount of about 5.5 to about 7 mg or about 6 to about 7 mg. In one aspect of this embodiment, doxepin is provided in an amount of about 6 mg. In another embodiment, SMCC is provided in an amount of about 94% w/w. The compositions disclosed herein can be in the form of a tablet, a film coated tablet, a capsule, a gel cap, a caplet, a pellet, a bead, or the like. In one embodiment, the compositions are in the form of tablets. In another embodiment, the compositions preferably are in the form of film coated tablets. In another embodiment, the compositions each have a total weight of about 50 mg to about 500 mg. In one aspect of this embodiment, the compositions each have a total weight of 50 mg, 75 mg, 100 mg, 150 mg, 200 mg, 250 mg, 300 mg, 350 mg, 400 mg, 450 mg, 500 mg, or the like. In one embodiment, the compositions each have a total weight of about 150 mg.

Embodiments of the invention also can include pharmaceutical compositions comprising from about 0.5 to about 9 mg of doxepin, or a pharmaceutically acceptable salt or prodrug thereof, and at least one filler. In one embodiment, the filler can be, for example, silicified microcrystalline cellulose, microcrystalline cellulose, lactose, a compressible sugar, xylitol, sorbitol, mannitol, pregelatinized starch, maltodextrin, calcium phosphate dibasic, calcium phosphate tribasic, calcium carbonate DC, a calcium silicate, a combinations of one or more of the same, or the like. In one aspect of this embodiment, the at least one filler can be silicified microcrystalline cellulose. The silicified microcrystalline cellulose can be provided in an amount of about 20% to about 99.9% w/w; of about 80% to about 99.8% w/w; or of about 94% to about 98.5% w/w, for example. The compositions can further comprise at least one of the following second fillers, microcrystalline cellulose, lactose, compressible sugars, xylitol, sorbitol, mannitol, pregelatinized starch, maltodextrin, calcium phosphate dibasic, calcium phosphate tribasic, calcium carbonate DC, a combinations of one or more of the same, or the like.

In one embodiment, the compositions further can comprise at least one glidant. In one aspect of this embodiment, the glidant can be, for example, colloidal silicon dioxide. In one embodiment, the colloidal silicon dioxide can be provided in an amount of about 0.1 to about 1.5% w/w, for example.

In one embodiment, the compositions further can comprise at least one lubricant. In one embodiment, the lubricant can be, for example, magnesium stearate, calcium stearate, sodium stearyl fumarate, stearic acid, hydrogenated vegetable oil, glyceryl behenate, polyethylene glycol, a combinations of one or more of the same, and the like. In one aspect of this embodiment, the lubricant can be magnesium stearate. In one embodiment, magnesium stearate can be provided, for example, in an amount of about 0.25 to about 1.5% w/w.

In one embodiment, the compositions further can comprise at least one disintegrant or at least one supplemental binder. In one aspect of this embodiment, the disintegrant can be, for example, croscarmellose sodium, sodium starch glycolate, crospovidone, microcrystalline cellulose, pregelatinized starch, corn starch, alginic acid, ion exchange resin, combinations of one or more of the same, and the like. In another embodiment, the supplemental binder can be, for example, hydroxypropyl cellulose, polyvinylpyrrolidone, methylcellulose, hydroxypropyl methylcellulose, ethylcellulose, or sodium carboxy methylcellulose, combinations of one or more of the same, and the like.

The compositions disclosed herein can be in the form of tablets, film coated tablets, capsules, gel caps, caplets, pellets, beads, or the like. The doxepin can be provided, for example, in an amount of about 0.5 mg to about 9 mg. Also, doxepin can be provided in an amount of about 1 to about 2 mg. In one embodiment, doxepin can be provided in an amount of about 1 mg. In another embodiment, doxepin can be provided in an amount of about 3 to about 4 mg. In another aspect, doxepin can be provided in an amount of about 3 mg. In another embodiment, doxepin can be provided in an amount of about 6 to about 7 mg. In one aspect of this embodiment, doxepin can be provided in an amount of about 6 mg.

Embodiments of the invention also provide compositions comprising from about 0.5 to about 9 mg doxepin having hardness values of at least 2 Kp, for example. In other embodiments, the compositions have hardness values of at least 4 Kp, at least 6 Kp, at least 8 Kp, at least 10 Kp or about 12 Kp, for example.

There is also provided a tablet, including a film coated tablet, comprising from about 0.5 to about 9 mg doxepin having a friability value of 1% or less, for example. In other embodiments, the tablet can have a friability value of about 0.75%, of about 0.5% or of about 0.25%, for example.

Embodiments of the invention also provide pharmaceutical compositions comprising from about 0.5 to about 9 mg doxepin having disintegration times of less than 1 minute per U.S. Pharmacopeia (USP) protocols (accessible on the world wide web and usp.org; the Pharmacopeia is incorporated herein by reference in its entirety), for example. In other embodiments, the compositions can have disintegration times of less than 30 seconds, of less than 20 seconds, of less than 10 seconds or of less than 6 seconds, for example.

Another embodiment provides pharmaceutical compositions comprising from about 0.5 to about 9 mg doxepin having at least an 85 percent release of doxepin within 30 minutes using U.S. Pharmacopeia (USP) Apparatus I at 100 rpm (or Apparatus II at 50 rpm) in 0.1 N HCl or Simulated Gastric Fluid USP without enzymes. In other embodiments, the composition can have, for example, at least an 85 percent release rate at 15 minutes, at least an 85 percent release rate at 10 minutes, at least an 85 percent release rate at 5 minutes, at least a 90 percent release rate at 30 minutes, at least a 95 percent release rate at 30 minutes. In some aspects of this embodiment, the compositions also can have at least an 85 percent release of doxepin within 30 minutes using U.S. Pharmacopeia (USP) Apparatus I at 100 rpm (or Apparatus II at 50 rpm) in a pH 4.5 buffer and/or at least an 85 percent release of doxepin within 30 minutes using U.S. Pharmacopeia (USP) Apparatus I at 100 rpm (or Apparatus II at 50 rpm) in a pH 6.8 buffer of Simulated Intestinal Fluid USP without enzymes.

Some embodiments of the invention provide pharmaceutical compositions comprising from about 0.5 to about 9 mg doxepin having at least an 85 percent release of doxepin within 30 minutes using U.S. Pharmacopeia (USP) Apparatus I at 100 rpm (or Apparatus II at 50 rpm) in a pH 4.5 buffer. In other embodiments, the compositions can have, for example, at least an 85 percent release rate at 15 minutes, at least an 85 percent release rate at 10 minutes, at least an 85 percent release rate at 5 minutes, at least a 90 percent release rate at 30 minutes or at least a 95 percent release rate at 30 minutes.

Another embodiment provides pharmaceutical compositions comprising from about 0.5 to about 9 mg doxepin having at least an 85 percent release of doxepin within 30 minutes using U.S. Pharmacopeia (USP) Apparatus I at 100 rpm (or Apparatus II at 50 rpm) in a pH 6.8 buffer or Simulated Intestinal Fluid USP without enzymes.

Embodiments of the invention also provide pharmaceutical compositions comprising about 0.5 to about 9 mg doxepin having two or more of the following characteristics: a hardness value of at least 2 Kp, a friability value of 1% or less, a disintegration time of less than 1 minute as per USP protocols, at least an 85 percent release of doxepin within 30 minutes using U.S. Pharmacopeia (USP) Apparatus I at 100 rpm (or Apparatus II at 50 rpm) in 0.1 N HCl or Simulated Gastric Fluid USP without enzymes, at least an 85 percent release of doxepin within 30 minutes using U.S. Pharmacopeia (USP) Apparatus I at 100 rpm (or Apparatus II at 50 rpm) in a pH 4.5 buffer, and at least an 85 percent release of doxepin within 30 minutes using U.S. Pharmacopeia (USP) Apparatus I at 100 rpm (or Apparatus II at 50 rpm) in a pH 6.8 buffer or Simulated Intestinal Fluid USP without enzymes.

Another embodiment provides a batch of unit dosage forms, each comprising from about 0.5 to about 9 mg doxepin, and the batch having content uniformity values between about 85% to 115% of a label claim. In other embodiments, the batch of unit dosage forms can have, for example, content uniformity values of between about 90% to 110% of label claim or of between about 95% to 105% of label claim. For example, the batch can comprise at least 50 unit dosage forms, e.g., tablets or film coated tablets.

In some embodiments the batch of unit dosage forms can comprise from about 100,000 to about 10,000,000 units, from about 500,000 to about 5,000,000 units, from about 1,000,000 to about 4,000,000 units, or from about 3,000,000 to about 4,000,000 units, for example. The units can be in the form of tablets, film coated tablets, capsules, caplets, pills, gel caps, pellets, beads, and the likes Embodiments of the invention also provide a batch of unit dosage forms, each comprising from about 0.5 to about 9 mg doxepin, having a content uniformity percent relative standard deviation of less than 5%. In other embodiments, the batch of unit dosage forms can have, for example, a content uniformity percent relative standard deviation of less than 4%, less than 3%, less than 2% or less than 1%.

Another embodiment provides a method of treating insomnia, comprising identifying an individual in need of such treatment, and administering any of the compositions disclosed herein to the individual.

Another embodiment relates to a method of treating insomnia, comprising identifying an individual in need of such treatment, providing the individual with instructions to take a doxepin dosage form according to any of the embodiments disclosed herein and providing any of the dosage forms disclosed herein to the individual.

Yet another embodiment provides a method of enhancing sleep maintenance, comprising identifying an individual in need of such enhancement, and administering any of the compositions disclosed herein to the individual.

Some embodiments provide methods of making a doxepin dosage form comprising combining from about 0.5 to about 9 mg doxepin and about 20% to about 99.9% silicified microcrystalline cellulose. In one embodiment, the silicified microcrystalline cellulose can be provided, for example, in amount of about 92% to about 99.8% w/w. The methods can further comprise adding from about 0.1 to about 1.5% w/w colloidal silicon dioxide and/or about 0.25 to about 1.5% w/w magnesium stearate. In other embodiments, doxepin can be provided in an amount of about 1 to about 2 mg, or about 3 to about 4 mg, or about 7 mg, for example. The silicified microcrystalline cellulose can be provided in amount of about 92% to about 99.8% w/w, of about 92% to about 99.8% w/w or of about 92% to about 99.8% w/w, for example. In another embodiment, doxepin and silicified microcrystalline cellulose can be combined with at least one filler selected from microcrystalline cellulose, lactose, compressible sugars, xylitol, sorbitol, mannitol, pregelatinized starch, maltodextrin, calcium phosphate dibasic, calcium phosphate tribasic, calcium carbonate DC, combinations of one or more of the same, and the like.

Embodiments of the invention also provide methods of making doxepin dosage forms comprising serially diluting and mixing a low concentration of doxepin with a higher concentration formulation excipient.

There is also provided a method of manufacturing a doxepin dosage form, wherein the method includes forming a drug substance pre-blend by mixing silicified microcrystalline cellulose and doxepin; forming a final blend by mixing silicified microcrystalline cellulose and the drug substance pre-blend; and forming a doxepin dosage form from the final blend. In one embodiment, the final blend can be compressed to form a doxepin tablet. The doxepin tablet also can be a film coated tablet. In some embodiments, the method can further comprise screening the drug substance pre-blend prior to forming the main blend. In another embodiment, the method further can comprise mixing the final blend for a time period sufficient to obtain a uniform distribution of doxepin prior to forming the tablet. In yet another embodiment, the method further can comprise mixing the final blend with magnesium stearate prior to forming the tablet. In some aspects the methods can include applying a coating to form a film coated tablet.

Another embodiment is a method of manufacturing a doxepin dosage form, wherein the method includes forming a drug substance pre-blend by mixing a first filler and doxepin; forming a final blend by mixing a second filler and the drug substance pre-blend; and forming a doxepin dosage form from the final blend. In one aspect of this embodiment, the first filler and the second filler can be, for example, silicified microcrystalline cellulose, microcrystalline cellulose, lactose, compressible sugars, xylitol, sorbitol, mannitol, pregelatinized starch, maltodextrin, calcium phosphate dibasic, calcium phosphate tribasic, calcium carbonate DC, combinations of one or more of the same, and the like. In one embodiment, the first and second fillers are not the same. In one embodiment, the first and/or the second filler can be silicified microcrystalline cellulose. In another embodiment, the first and second fillers can be the same. In yet another embodiment, the first and the second filler can be silicified microcrystalline cellulose. In another embodiment, the drug substance pre-blend or the final blend can comprise an additional filler. The additional filler can be, for example, silicified microcrystalline cellulose, microcrystalline cellulose, lactose, compressible sugars, xylitol, sorbitol, mannitol, pregelatinized starch, maltodextrin, calcium phosphate dibasic, calcium phosphate tribasic, calcium carbonate DC, combinations of one or more of the same, and the like.

Embodiments of the invention also provide methods of manufacturing a doxepin dosage form by direct compression. The methods can include, for example, forming a color blend by mixing one or more pharmaceutically acceptable colorants and silicified microcrystalline cellulose; forming an initial drug substance pre-blend by mixing silicified microcrystalline cellulose and doxepin; forming a final drug substance pre-blend by mixing the color blend and initial drug substance pre-blend; screening the final drug-substance pre-blend; forming a main blend by mixing silicified microcrystalline cellulose and the final drug-substance pre-blend; mixing the main blend for a time period sufficient to obtain a uniform distribution of doxepin; forming a final blend by mixing a lubricant and the main blend; and forming the final blend into a doxepin dosage form.

In one aspect of this embodiment, forming the initial drug substance pre-blend can comprise sequentially screening a first portion of the silicified microcrystalline cellulose, screening the doxepin, and screening a second portion of the silicified microcrystalline cellulose. In some aspects, the methods preferably can include methods to prevent re-agglomeration of the materials. For example, the screened powders can be placed into a blender and mixed, and the initial drug substance pre-blend can be screened using a vibrating sieve, a cone mill or a co mill, which operate in manner that prevents re-agglomeration of cohesive powders. In another embodiment, forming the final drug substance pre-blend can comprise sequentially adding a first portion of the color pre-blend or filler, adding the initial drug substance pre-blend, and adding a second portion of the color pre-blend or filler. In another embodiment, the final drug substance pre-blend can comprise combining two, equivalent initial drug substance pre-blends.

In another embodiment, color can be imparted with a tablet coating process which obviates the need for a color pre-blend. For the low dose embodiments, in some aspects the absence of a color pre-blend can result in the preparation of only one drug substance pre-blend rather than an initial and final drug substance pre-blend. In some embodiments, screening the final drug-substance pre-blend step can be repeated prior to forming the main blend. In another embodiment, screening the final drug-substance pre-blend can comprise using a vibrating sieve. In aspects of this embodiment, the final drug-substance pre-blend can be screened using a vibrating sieve, for example, equipped with a 10 to 200 mesh screen, a 20 to 80 mesh screen, or a 30 mesh screen, or the like. In some embodiments, forming the main blend can comprise sequentially adding a first portion of the silicified microcrystalline cellulose, adding the drug-substance pre-blend, and adding a second portion of the silicified microcrystalline cellulose. In other embodiments, the main blend can be mixed, for example, for about 5 to about 60 minutes, for about 10 to about 40 minutes or for about 20 minutes. In one embodiment, the main blend can be mixed, for example, in an in-bin blender. The lubricant can be, for example, magnesium stearate, calcium stearate, sodium stearyl fumarate, stearic acid, hydrogenated vegetable oil, glyceryl behenate, polyethylene glycol, combinations of one or more of the same, and the like. In one embodiment, the lubricant can comprise magnesium stearate. In some embodiments, the final blend can be compressed to form the tablet, for example.

Another embodiment provides a method of preparing a uniform low-dose doxepin pre-blend comprising serially diluting and mixing a low concentration of doxepin with higher concentration formulation excipients.

Embodiments of the invention also provide methods of making a plurality of doxepin dosage forms. The methods can include, for example, providing an amount of doxepin to obtain a plurality of doxepin tablets, including film coated tablets, wherein each tablet comprises between about 0.1 mg to 9 mg of doxepin; providing one or more excipients; mixing said doxepin and excipients such that the plurality of doxepin dosage forms comprises at least one of content uniformity values between about 85% and 115% of label claim or a content uniformity percent relative standard deviation of less than 5%. In other embodiments, the plurality of dosage forms can comprise content uniformity values between about 90% to 110% of label claim, or between about 95% to 105% of a label claim, for example. In other embodiments, the plurality of dosage forms can comprise a content uniformity percent relative standard deviation of less than 5%, of less than 4 of less than 3%, of less than 2%, or of less than 1%, for example.

In one aspect of this embodiment, the one or more excipients can comprise SMCC. The one or more excipients can further comprise an excipient, such as, for example, microcrystalline cellulose, lactose, a compressible sugar, xylitol, sorbitol, mannitol, pregelatinized starch, maltodextrin, calcium phosphate dibasic, calcium phosphate tribasic, calcium carbonate DC, a calcium silicate, and the like. In another embodiment, the one or more excipients can comprise, for example, between about 20% and 100% SMCC. In other embodiments, the plurality of dosage forms can comprise, for example, from about 100,000 to about 10,000,000 units, from about 500,000 to about 5,000,000 units, from about 1,000,000 to about 4,000,000 units or from about 3,000,000 to about 4,000,000 units.

Some embodiments relate to pharmaceutical unit dosage form, comprising doxepin, a pharmaceutically-acceptable salt or prodrug thereof in an amount equivalent to about 1 mg doxepin hydrochloride; one or more pharmaceutically-acceptable excipients; and optionally, a capsule or coating. In some embodiments, the excipients and any capsule or coating can be selected to provide a swallowable unit dosage that is at least externally solid and that has dissolution and bioavailablity characteristics such that after administration to a 70 kg human, the dosage form provides a plasma concentration of at least 0.05 ng/mL doxepin within a time frame of not more than about 90 minutes, for example. The dosage form can be a tablet, a film coated tablet, a capsule, a pill, a caplet, a gel cap, a pellet, a bead, or a dragee. In one embodiment, the dosage form can be a tablet. In some embodiments, the dosage form preferably can be a film coated tablet. In another embodiment, the dosage form can be a capsule. In yet another embodiment, the time frame to provide a plasma concentration of at least 0.05 ng/mL is not more than about 80 minutes, for example.

Another embodiment of the invention is directed to a pharmaceutical unit dosage form, comprising doxepin, a pharmaceutically-acceptable salt or prodrug thereof in an amount equivalent to about 1 mg, 3 mg, or 6 mg doxepin hydrochloride; one or more pharmaceutically-acceptable excipients; and optionally, a capsule or coating. In some embodiments, the excipients and any capsule or coating can be selected to provide a swallowable unit dosage that is at least externally solid and that has dissolution and bioavailablity characteristics such that after administration to a 70 kg human, the dosage form provides a plasma concentration of at least 0.1 ng/mL doxepin within a time frame of not more than about 60 minutes. In yet another embodiment, the time frame to provide a plasma concentration of at least 0.1 ng/mL is not more than about 50 minutes. In some aspects, the dosage form can provide a plasma concentration of at least 0.05 ng/mL doxepin within a time frame of not more than about 90 minutes, for example. The dosage form can be a tablet, a film coated tablet, a capsule, a pill, a caplet, a gel cap, a pellet, a bead, or a dragee. In one embodiment, the dosage form can be a tablet. In some embodiments, the dosage form preferably can be a film coated tablet. In another embodiment, the dosage form can be a capsule.

Some embodiments relate to pharmaceutical compositions comprising 0.5 to 9 mg doxepin or a pharmaceutically acceptable salt or prodrug of doxepin where the composition comprises at least two or more of the characteristics of: a hardness value of at least 2 Kp, a friability value of 1% or less, a disintegration time of less than 1 minute as per U.S. Pharmacopeia (USP) protocols, at least an 80% release of doxepin within 15 minutes using compendial method for measuring dissolution of doxepin. Preferably, the compositions comprise at least 80% release of doxepin within 15 minutes. Also, some embodiments relate to compositions or formulations that release at least from about 60% to about 99.5% doxepin after about 5 to about 40 minutes. The release or dissolution can be determined using the USP-based methods. Preferably, 60%, 65%, 70%, 75%, 80%, 85%, 90%, 95% or 99.5% doxepin is released after 3, 5, 10, 15 or 30 minutes, for example. Thus, some embodiments relate to low dose doxepin formulations that have the unexpected dissolution properties listed above and elsewhere herein.

Some embodiments relate to methods for processing or producing low dose doxepin dosage forms, for example, from about 0.5 mg to about 9 mg doxepin, while obtaining high content uniformity. The methods can include minimizing segregation of low dose doxepin, which segregation can cause a lack of uniformity of dosage forms, by minimizing fluidization of low dose doxepin blended with a filler, including any of the fillers listed herein. In some embodiments, the minimizing of fluidization can be accomplished by minimizing airflow through a blend of low dose doxepin and one more fillers. Examples of minimizing airflow can include providing vents, valves or other devices that permit the release of air from containment devices that transport or hold the low dose doxepin blend. Also, fluidization can be minimized by reducing the amount of airspace in a dosage form press, such that there is less opportunity for contact of the blend with air. Also, the low dose formulations can be produced using a wet granulation method in order to avoid fluidization. Furthermore, carriers or fillers that bind with greater strength to the doxepin can be utilized. Such carriers/fillers can be easily incorporated by one of skill in the art.

Also, content uniformity can be maintained or enhanced by minimizing agglomeration or re-agglomeration of doxepin in the low dose doxepin formulations. Examples of minimizing agglomeration are described herein. Such methods can include, for example, diluting or layering the low dose doxepin with one or more fillers (including those listed or described herein). The methods can also include the use of a cone mill, a co mill or the like, including devices that minimize the separation of the doxepin from filler blends and dilution blends/mixes.

DETAILED DESCRIPTION

Figure 1:
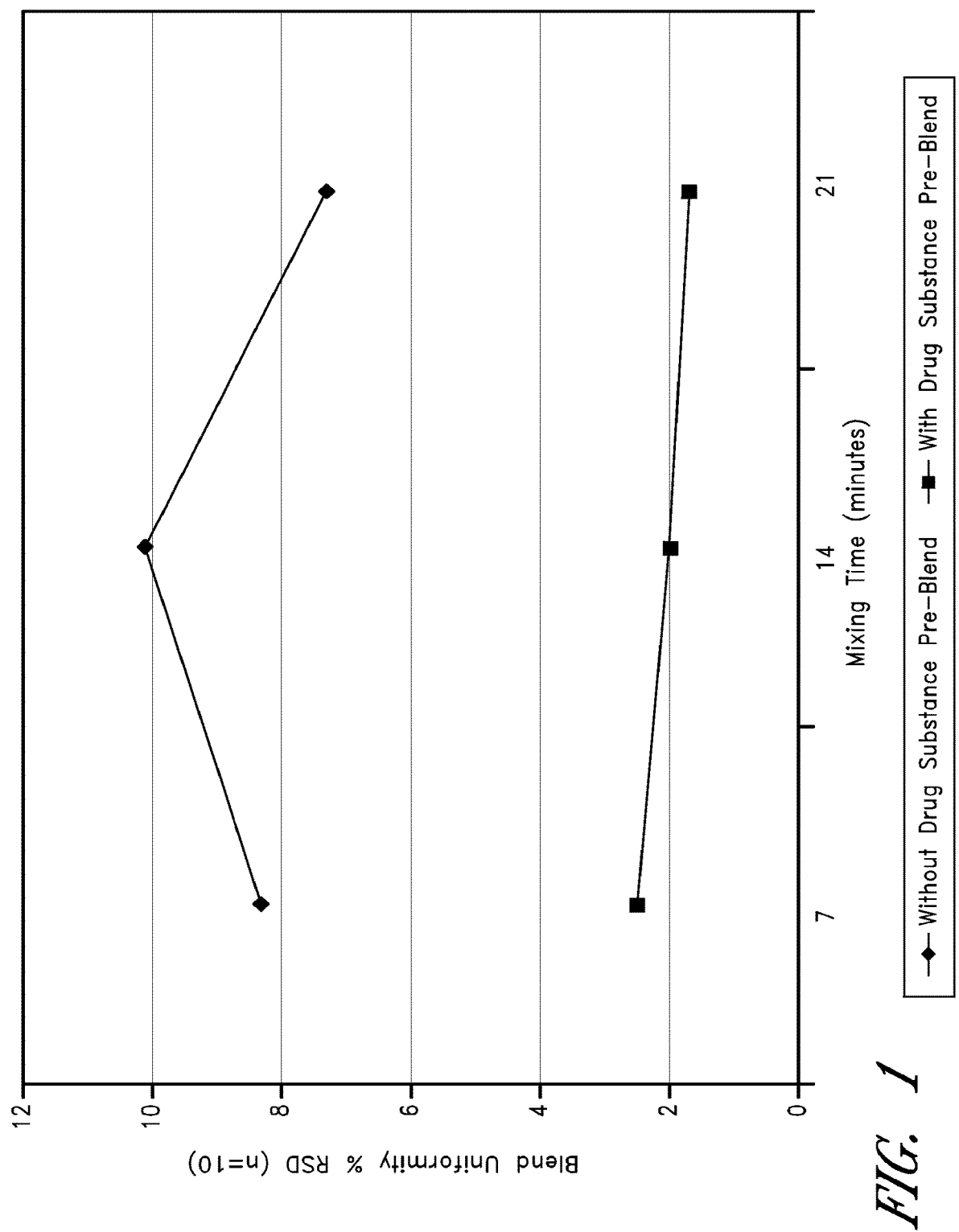
FIG. 1 is a graph showing the blend uniformity with and without drug substance pre-blend.

Embodiments of the invention generally relate to new and surprisingly effective doxepin formulations and methods of using low-dose forms of doxepin, including, for example, use in the treatment of insomnia. Also, some embodiments of this invention relate to novel and economical methods of manufacturing low-dose dosage forms of doxepin, pharmaceutically acceptable salts thereof, or prodrugs thereof.

Doxepin is a tricyclic compound currently approved for treatment of depression or anxiety at a daily dose of 75 mg to 300 mg. Doxepin is marketed under the commercial name SINEQUAN® and in generic form, and can be obtained in the United States generally from pharmacies in capsule form in amounts of 10, 25, 50, 75, 100 and 150 mg dosage, and in liquid concentrate form at 10 mg/mL. The capsule formulations contain Doxepin HCl with cornstarch and magnesium stearate/sodium lauryl sulfate. Capsule shells can also contain gelatin, sodium lauryl sulfate, sodium metabisulfate and colorants. Such capsule formulations or formulations using one or more of the features of the capsule formulations can be specifically excluded from some embodiments herein. For example, doxepin formulations comprising starch and/or a gelatin shell can be exclude from some embodiments.

The use of low dose doxepin for the treatment of insomnia is described in U.S. Pat. Nos. 5,502,047 and 6,211,229, the entire contents of which are incorporated herein by reference. As mentioned above, many individuals currently suffer from sleep disorders, such as insomnia. There is a need for improved compositions and methods for treating such individuals.

Compounds
Doxepin
Doxepin HCl is a tricyclic compound currently approved and available for treatment of depression and anxiety.

Doxepin belongs to a class of psychotherapeutic agents known as dibenzoxepin tricyclic compounds, and is currently approved and prescribed for use as an antidepressant to treat depression and anxiety. Doxepin has a well-established safety profile, having been prescribed for over 35 years.

It is contemplated that doxepin for use in the compositions and methods described herein can be obtained from any suitable source or made by any suitable method. For example, doxepin HCl can be obtained from Plantex Ltd. (DMF No. 3230). In the Biopharmaceutic Classification System, doxepin HCl, USP is designated as a Class One compound, with high solubility and high permeability. The Plantex-supplied doxepin HCl, USP has a particle size specification of not less than 80% smaller than 38 microns and not less than 90% smaller than 125 microns as measured by an Air Jet Sieve method.

Also, doxepin can be prepared according to the method described in U.S. Pat. No. 3,438,981, which is incorporated herein by reference in its entirety. As another illustration, doxepin can be prepared from 11-[3-(Dimethylamino)propyl]-6,11-dihydrodibenzo[b,e]oxepin-11-ol as taught in U.S. Pat. No. 3,420,851, which is incorporated herein by reference in its entirety. It should be noted and understood that although many of the embodiments described herein specifically refer to "doxepin," other doxepin-related compounds can also be used, including, for example, pharmaceutically acceptable salts, prodrugs, in-situ salts of doxepin formed after administration, and solid state forms, including polymorphs and hydrates.

Pharmaceutically Acceptable Salts:

As mentioned above, the methods and other embodiments described herein can utilize any suitable pharmaceutically acceptable salt or prodrug of doxepin. Therefore, the substitution or use in combination of salts and prodrugs is specifically contemplated in the embodiments described herein. The pharmaceutically acceptable salts and prodrugs can be made by any suitable method.

The term "pharmaceutically acceptable salt" refers to an ionic form of a compound that does not cause significant irritation to an organism to which it is administered and does not abrogate the biological activity and properties of the compound. Pharmaceutical salts can be obtained by reacting a compound, for example, doxepin, with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like. Pharmaceutically acceptable salts are more fully described in the following paragraph.

The acids that can be used to prepare pharmaceutically acceptable acid addition salts include, for example, those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, dislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The bases that can be used to prepare pharmaceutically acceptable base addition salts include, for example, those that form non-toxic base addition salts, i.e., base salts formed with metals or amines, such as alkali and alkaline earth metals or organic amines. Non-limiting examples of metals used as cations include sodium, potassium, magnesium, calcium, and the like. Also included are heavy metal salts such as for example silver, zinc, cobalt, and cerium. Non-limiting examples of suitable amines include N,N'-dibenzylethylenediamine, chloroprocaine, choline, diethanolamine, ethylenediamene, N-methylglucamine, and procaine.

Prodrugs:

The term "prodrug" refers to an agent that is converted into the active drug in vivo. Prodrugs are often useful because, in some situations, they can be easier to administer than the active drug. They can, for instance, be bioavailable by oral administration whereas the active drug is not. The prodrug may also have improved solubility in pharmaceutical compositions over the active drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Examples of prodrug groups can be found in, for example, T. Higuchi and V. Stella, in "Pro-drugs as Novel Delivery Systems," Vol. 14, A.C.S. Symposium Series, American Chemical Society (1975); H. Bundgaard, "Design of Prodrugs," Elsevier Science, 1985; and "Bioreversible Carriers in Drug Design: Theory and Application," edited by E. B. Roche, Pergamon Press: New York, 14-21 (1987), each of which is hereby incorporated by reference in its entirety.

Compositions

Dosage form development requires the selection of excipients based on the properties of the drug substance being formulated. Several preferred embodiments of this invention are provided. These should not be construed as limiting the scope of this invention.

Some embodiments of the invention are based upon the new discovery of previously unknown physical characteristics and challenges associated with low-dose doxepin compositions, and also upon a new understanding of pharmacokinetics of doxepin when it is used to treat sleep disorders.

For example, it has been found that formulation of compositions at the lower dose range can present a considerable challenge in maintaining consistent potency and uniformity in the drug product manufacturing process, while also maintaining a high yield. For example, assuring the homogeneity of the powder blend for production of low-dose dosage forms can represent a major quality assurance consideration. The selection of the particular excipient or excipients used, and how to properly blend and prevent non-uniformity and segregation were based upon previously unrecognized characteristics and needs for doxepin formulation, particularly low-dose formulations.

Also, in some embodiments, the compositions are based upon previously unknown pharmacokinetics of low-dose doxepin for sleep. Although doxepin dissolves quickly in the stomach, it can take some time for the sleep promoting action of the drug to take place. No one previously recognized the sleep pharmacokinetics of doxepin, such as, sleep onset characteristics of doxepin; and for sleep, even decreasing induction time by a few minutes can provide an enormous benefit. In the context of sleep, early onset of drug action can be important due to the discreet window of time (e.g., 8 hours) in which a patient needs to sleep. As a consequence, some embodiments relate to compositions that can contribute to accelerated action of the drug. That need was not recognized previously, in particular for depression and anxiety where there was no need for fast onset due to the ongoing and chronic nature of those conditions. The unique needs of doxepin for treating sleep were not appreciated in the prior art.

Accordingly, some embodiments relate to compositions for the treatment of such disorders where careful selection of excipients was used to address the previously unrecognized characteristics of low-dose doxepin and doxepin for use in treating sleep disorders. Described below and elsewhere herein are new and unexpectedly effective doxepin formulations.

Doxepin HCl, USP, is a white crystalline powder with a slight amine-like odor supplied by Plantex Ltd. In the Biopharmaceutic Classification System, doxepin HCl, USP is designated as a Class One compound, with high solubility and high permeability (Wu-Benet, 2005). The Plantex-supplied doxepin HCl, USP has a particle size specification of not less than 80% smaller than 38 microns and not less than 90% smaller than 125 microns as measured by an Air Jet Sieve method.

In a preferred embodiment, the compositions disclosed herein can include from about 0.01 mg to about 9 mg of doxepin, or from about 0.5 mg to about 7 mg doxepin, or from about 1 mg to about 6 mg doxepin. In some embodiments, the compositions include from about 0.5 mg to about 2 mg doxepin, or from about 2.5 mg to about 4 mg, or from about 5.9 mg to about 7 mg doxepin.

As discussed above, in some embodiments, doxepin prodrugs or pharmaceutically acceptable salts of doxepin can be used in place of, or in addition to, low-dose doxepin in the formulations described herein.

Some embodiments provide low-dose doxepin tablets, film coated tablets, capsules, caplets, pills, gel caps, pellets, beads, or dragee dosage forms. Some embodiments specifically exclude one or more such dosage forms.

Preferably, the formulations disclosed herein can provide favorable drug processing qualities, including, for example, but not limited to, rapid tablet press speeds, reduced compression force, reduced ejection forces, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation. Many of these qualities, notably, content uniformity and blend uniformity, are difficult to obtain in low dose formulations.

Making the drug available for absorption with minimal delay can be important in the treatment of medical conditions such as insomnia. In a preferred embodiment, the formulations can yield extremely rapid disintegration times of 1 minute or less as per USP protocols. Preferably, the formulation yields disintegration times of 50, 40, 30, 25, 10 seconds or less. More preferably, the formulation yields dosage form disintegration times of 8 seconds or less, and even more preferably 6 seconds or less. In a preferred embodiment, silicified microcrystalline cellulose (SMCC), e.g., Prosolv SMCC® (JRS Pharma Inc., Patterson, N.Y.) is used as a diluent or filler to impart favorable disintegration times.

In other embodiments, the formulation yields a rapidly dissolving dosage form, for which at least 85% of the labeled amount of the drug substance dissolves within 30 minutes, using U.S. Pharmacopeia (USP) Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes.

In some embodiments, the formulations require minimal tablet compression forces to achieve a hardness of about 2 to about 25 kp. In some aspects, the formulation can require compression forces to achieve a hardness of, for example, at least 2, 3, 4, 5, 6, 7, 8, 9, 10, 11, 12, 15, 18, 20 or 21 kp. Such minimal compression forces can enables the tablets to remain relatively porous and disintegrate fast with minimal wear on compression tooling and the tablet press. In one embodiment of the invention disclosed herein, the use of SMCC as a diluent imparts favorable compressibility and disintegration of the dosage form.

In other embodiments, the formulations can yield tablets, including film coated tablets, having a friability value of 1% or less. Thus, in some embodiments, the friability value is about 0.9%, 0.8%, 0/75%, 0.6%, 0.5%, 0.4%, 0.3%, 0.25% or less.

Preferably, the formulations disclosed herein provide a batch of low-dose doxepin dosage forms having content uniformity values between about 75% to about 125% of label claim, or from about 85% to about 115% of label claim, more preferably between about 90% to about 110% of label claim, and more preferably between about 95% to about 105% of label claim. In some embodiments, the formulations yield a batch of low-dose doxepin dosage forms having a content uniformity percent relative standard deviation of 7.8% or less. In some embodiments, the relative standard deviation is equal to or less than 6%, 5%, 4%, 3%, 2%, or 1%. Preferably, the formulations disclosed herein provide a high yield of low-dose doxepin dosage forms having acceptable content uniformity. The batch can include, for example, about from about 50 to about 5,000,000 unit dosage forms or any amount in between, or even more if desired.

In other preferred embodiments, tablet ejection forces are very low enabling lubrication levels to be kept low and preventing adverse effects due to over lubrication, including, for example, soft tablets, retarded dissolution, etc. This further reduces wear on compression tooling. In a preferred embodiment, the use of SMCC permits the use of low ejection forces.

In some embodiments, the product does not exhibit a sensitivity of product performance (tablet hardness and dissolution) to the lubricant blend time. For example, in one embodiment the SMCC based formulation unexpectedly and surprisingly is resistant to the impact of over-lubrication normally associated with magnesium stearate. In many cases, lubricant blend time can affect product performance. Very surprisingly, here lubrication with magnesium stearate can result in low dose doxepin formulations that are resistant to the normal over-lubrication effects.

In a preferred embodiment, the low-dose dosage forms described herein are formulated to yield two or more favorable drug characteristics.

The compounds can be formulated readily, for example, by combining the drug substance with any suitable pharmaceutically acceptable excipient for example, but not limited to, binders, diluents, disintegrants, lubricants, fillers, carriers, and the like, as set forth below. Such compositions can be prepared for storage and for subsequent processing.

Acceptable excipients for therapeutic use are well known in the pharmaceutical art, and are described, for example, in Handbook of Pharmaceutical Excipients, 5th edition (Raymond C Rowe, Paul J Sheskey and Siân C Owen, eds. 2005), and Remington: The Science and Practice of Pharmacy, 21st edition (Lippincott Williams & Wilkins, 2005), each of which is hereby incorporated in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule, tablet, film coated tablet, caplet, gel cap, pill, pellet, bead, and the like suitable for oral administration. Excipients can include, by way of illustration and not limitation, diluents, disintegrants, binding agents, wetting agents, polymers, lubricants, glidants, substances added to mask or counteract a disagreeable taste or odor, flavors, colorants, fragrances, and substances added to improve appearance of the composition.

Acceptable excipients include, for example, but are not limited to, SMCC, microcrystalline cellulose, lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. The compound can also be made in microencapsulated form. If desired, absorption enhancing preparations (for example, liposomes), can be utilized.

The compositions and formulations can include any other agents that provide improved transfer, delivery, tolerance, and the like. These compositions and formulations can include, for example, powders, pastes, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Any of the foregoing mixtures can be appropriate in treatments and therapies in accordance with the invention disclosed herein, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Charman W N "Lipids, lipophilic drugs, and oral drug delivery-some emerging concepts." J Pharm Sci. 89(8):967-78 (2000), and the citations therein for additional information related to formulations, excipients and carriers well known to pharmaceutical chemists.

In some embodiments, one or more, or any combination of the listed excipients can be specifically included or excluded from the formulations and/or methods disclosed herein. For example, in some embodiments, microcrystalline cellulose can be specifically excluded.

The formulation can be in form suitable for bolus administration, for example. Oral administration can be accomplished using orally administered formulations, for example, tablets, film coated tablets, capsules, gel caps, caplets, pellets, beads, pills, and the like. In addition, stabilizers can be added. All formulations for oral administration should be in dosages suitable for such administration.

As will be appreciated by those of skill in the art, the amounts of excipients will be determined by drug dosage and dosage form size. In some embodiments disclosed herein, the dosage form size is 150 mg. This dosage form weight is arbitrary and one skilled in the art will realize that a range of weights can be made and are encompassed by this invention. The preferred dosage form range is 50 mg to 500 mg, more preferably 75 mg to 300 mg, more preferably 100 to 200 mg, with the preferred dosage form weight being 150 mg.

In some embodiments, a high functionality excipient can be used in the formulations. The term "high functionality excipient" is defined as an inactive ingredient that meets the following four criteria: (1) multifunctional in that one excipient contributes two or more functions to a formulation, (2) high inherent functional performance even at low use levels, allowing for increased batch sizes and higher drug loading (3) does not require complex processing steps, making it ideal for cost effective direct compression processes and (4) imparts high inherent functional performance to the overall formulation. High functionality excipients provide the means for simplifying formulation development, and improving overall operational costs while preserving the quality that is essential for pharmaceutical products.

In a preferred embodiment, low doses of doxepin are combined with silicified microcrystalline cellulose (SMCC), e.g., Prosolv SMCC® (JRS Pharma Inc., Patterson, N.Y.). For example, based on a 150 mg dosage form weight, the range of drug substance is from about 0.75% to about 4.5% w/w and the range of SMCC is from about 90 to 99.8% w/w, or from about 92% to about 99% w/w, or from about 94% to about 98.5% w/w.

"Silicified microcrystalline cellulose," also referred to by the acronym "SMCC", is composed of 98% microcrystalline cellulose USP/NF and 2% colloidal silicon dioxide USP/NF. The silicification of the microcrystalline cellulose forms an intimate association between the colloidal silicon dioxide and the microcrystalline cellulose. SMCC provides the role of a high functionality excipient and imparts the functions of diluent, binder and/or disintegrant. The use of SMCC is disclosed in U.S. Pat. Nos. 5,585,115, 5,725,884, 5,866,166, 6,217,909, 6,358,533, 6,471,994, 6,521,261, 6,476,693, 6,936,277, each of which is hereby incorporated by reference in its entirety. Several grades of SMCC are currently available, with particle size and bulk density being a principle differentiating properties among the grades. Preferably, the particle size of the diluent can be selected based on consideration of the particle size of the drug substance. In one embodiment of the invention disclosed herein, the particular grade has a median particle size (by sieve analysis) of approximately 90 µm.

The silicified microcrystalline cellulose used in the preparations disclosed herein can be any combination of microcrystalline cellulose co-processed with colloidal silicon dioxide, including, for example, that which can be obtained commercially from JRS Pharma Inc. under the name ProSolv SMCC®. There are different grades of SMCC available, with particle size and bulk density being exemplary differentiating properties among the grades. It should be noted that as described below, other excipients can be used in combination with or substituted for SMCC in order to formulate suitable doxepin dosage forms.

The use of SMCC as a diluent or filler imparts favorable drug processing qualities, including, for example, but not limited to, rapid tablet press speeds, reduced compression force, reduced ejection force, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation.

In addition, SMCC is easily compacted (an efficient binder) and possesses effective disintegration properties. These two characteristics create hard tablets that rapidly dissolve. In some embodiments, SMCC is also used to serially dilute the drug substance and colorants to promote their uniform distribution in the formulation as well as to dry-rinse the equipment surfaces to minimize any potential loss of drug substance during the manufacturing process.

In one embodiment, a dry pharmaceutical blend of silicified microcrystalline cellulose and low-dose doxepin, or a low-dose doxepin-related compound, is used to produce the final dosage form by direct compression. Typically, the dry blend contains from about 0.1% to about 10% w/w, or from about 0.5% to about 5% w/w, or from about 0.7% to about 4.5% w/w of low-dose doxepin or a low-dose doxepin-related compound. In one embodiment, the doxepin or doxepin-related compound, in the dry blend is non-granulated. In addition to doxepin, the blend can contain from about 20% to about 99.9% w/w SMCC, or from about 50% to about 99.5% w/w SMCC, or from about 75% to about 99% w/w SMCC, or from about 80% to about 98.7% SMCC, or from about 92% to about 98.5% w/w SMCC, or from about 94% to about 98% w/w SMCC.

In some embodiments, SMCC can be combined or replaced with one or more of the following excipients: microcrystalline cellulose, lactose monohydrate (spray dried), a compressible sugar, xylitol (Xylitab), sorbitol, mannitol, pregelatinized starch, maltodextrin, calcium phosphate dibasic, calcium phosphate tribasic, calcium carbonate DC, and the like. Accordingly, in one embodiment, one or more of the above excipients can be combined with SMCC in various ratios. For example, assuming the total filler to be 100%, about 80% SMCC can be combined with about 20% of one or more alternate filler(s). Alternatively, about 70% SMCC can be combined with about 30% of one or more alternate filler(s), or about 60% SMCC can be combined with about 40% of one or more alternate filler(s), or about 50% SMCC can be combined with about 50% of one or more alternate filler(s), or about 40% SMCC can be combined with about 60% of one or more alternate filler(s), or about 30% SMCC can be combined with about 70% of one or more alternate filler(s), or about 20% SMCC can be combined with about 80% of one or more alternate filler(s).

In alternate embodiments, SMCC can be replaced with one or more alternate excipients. Preferably, alternate excipients are selected to provide favorable drug processing qualities. For example, in one embodiment a 50:50 ratio of microcrystalline cellulose to lactose can be used in place of SMCC. In this example, the overall compressibility of the lactose would be improved allowing for less compression force resulting in a more porous tablet, film coated tablet, caplet, pellet, bead, or pill that can show improved dissolution over the microcrystalline cellulose or lactose alone. Other favorable excipient combinations will be apparent to one of skill in the art.

The dry blend can also include at least one additional suitable pharmaceutically acceptable excipient. Additional excipients can include processing aids that improve the direct compression tablet-forming properties of the dry blend, and/or powder flowability. In the dry blend, excipients suitable for use in direct compression include, but are not limited to, binders, diluents, disintegrants, lubricants, fillers, carriers, and the like as set forth above.

In one embodiment, the formulation comprises a mixture of the drug substance with SMCC, and additional processing aides, such as, for example, magnesium stearate and colloidal silicon dioxide, and optionally, colorant(s). For example, in some embodiments, colloidal silicon dioxide, which is a component of SMCC, is also added separately to the formulation as a glidant to facilitate mass flow of the powder mixture during blending and tablet compression operations. Colloidal silicon dioxide can be added at concentrations ranging from about 0.1% to about 5.0% w/w, or from about 0.25% to about 2% w/w, or from about 0.5% to about 1% w/w.

In some embodiments, magnesium stearate can be added as a lubricant, for example, to improve powder flow, prevent the blend from adhering to tableting equipment and punch surfaces and provide lubrication to allow tablets to be cleanly ejected from tablet dies. Magnesium stearate can typically be added to pharmaceutical formulations at concentrations ranging from about 0.1% to about 5.0% w/w, or from about 0.25% to about 2% w/w, or from about 0.5% to about 1% w/w.

In some embodiments, color additives also can be included. The colorants can be used in amounts sufficient to distinguish dosage form strengths. Preferably, color additives approved for use in drugs (21 CFR 74, which is incorporated herein by reference in its entirety) are added to the commercial formulations to differentiate tablet strengths. The use of other pharmaceutically acceptable colorants and combinations thereof are encompassed by the current invention.

Binders can be used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, cellulosic polymers (including, for example, hydroxypropyl cellulose, hydroxypropyl methylcellulose, methyl cellulose, hydroxyethyl cellulose, and the like).

Accordingly, in some embodiments, the formulations disclosed herein can include at least one binder to enhance the compressibility of the major excipient(s). For example, the formulation can include at least one of the following binders in the following preferred ranges: from about 2 to about 6% w/w hydroxypropyl cellulose (Klucel), from about 2 to about 5% w/w polyvinylpyrrolidone (PVP), from about 1 to about 5% w/w methycellulose, from about 2 to about 5% hydroxypropyl methylcellulose, from about 1 to about 5% w/w ethylcellulose, from about 1 to about 5% w/w sodium carboxy methylcellulose, and the like. The above ranges are exemplary preferred ranges. One of ordinary skill in the art would recognize additional binders and/or amounts that can be used in the formulations described herein. As would be recognized by one of ordinary skill in the art, when incorporated into the formulations disclosed herein, the amounts of the major filler(s) and/or other excipients can be reduced accordingly to accommodate the amount of binder added in order to keep the overall unit weight of the tablet unchanged. In one embodiment, the binder(s) is(are) sprayed on from solution, e.g. wet granulation, to increase binding activity.

Lubricants can be employed herein in the manufacture of certain dosage forms. For example, a lubricant will often be employed when producing tablets. In an embodiment of the invention disclosed, a lubricant can be added just before the tableting step, and can be mixed with the formulation for a minimum period of time to obtain good dispersal. In some embodiments, one or more lubricants can be used. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax® for polyethylene glycol and Polyox® for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Preferred lubricants are magnesium stearate, calcium stearate, zinc stearate and mixtures of magnesium stearate with sodium lauryl sulfate. Lubricants can comprise from about 0.25% to about 10% of the tablet weight, more preferably from about 0.5% to about 3%.

Thus, in some embodiments, the formulations disclosed herein can include at least one lubricant in the following preferred ranges: from about 0.25 to about 2% w/w magnesium stearate, from about 0.25 to about 2% w/w calcium stearate, from about 0.25 to about 2% w/w sodium stearyl fumarate, from about 0.25 to about 2% w/w stearic acid, from about 0.25 to about 2% w/w hydrogenated vegetable oil, from about 0.25 to about 2% w/w glyceryl behenate, from about 0.25 to about 2% w/w polyethylene glycol 4000-6000, and the like. The above ranges are examples of preferred ranges. One of ordinary skill in the art would recognize additional lubricants and/or amounts that can be used in the formulations described herein. As would be recognized by one of ordinary skill in the art, when incorporated into the formulations disclosed herein, the amounts of the major filler(s) and/or other excipients can be reduced accordingly to accommodate the amount of lubricant(s) added in order to keep the overall unit weight of the tablet unchanged.

Disintegrants can be used, for example, to facilitate tablet disintegration after administration, and are generally starches, clays, celluloses, algins, gums or crosslinked polymers. Suitable disintegrants include, but are not limited to, crosslinked polyvinylpyrrolidone (PVP-XL), sodium starch glycolate, and croscarmellose sodium. If desired, the pharmaceutical formulation can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc. and the like.

In some embodiments, at least one additional disintegrant can be included in the following preferred ranges: from about 1 to about 3% w/w croscarmellose sodium, from about 4 to about 6% w/w sodium starch glycolate, from about 2 to about 4% w/w crospovidone, from about 10 to about 20% w/w microcrystalline cellulose, from about 5 to about 10% w/w pregelatinized starch, from about 5 to about 10% w/w corn starch, from about 5 to about 10% w/w alginic acid, from about 1 to about 5% w/w ion exchange resin (Amberlite 88), and the like. The above ranges are examples of preferred ranges. One of ordinary skill in the art would recognize additional disintegrants and/or amounts of disintegrants that can be used in the formulations described herein. As would be recognized by one of ordinary skill in the art, when incorporated into the formulations disclosed herein, the amounts of the major filler(s) and/or other excipients can be reduced accordingly to accommodate the amount of disintegrant added in order to keep the overall unit weight of the tablet unchanged.

In some embodiments, the formulations can include a coating, for example, a film coating. Where film coatings are involved, coating preparations can include, for example, a film-forming polymer, a plasticizer, or the like. Also, the coatings can include pigments and/or opacifiers. Non-limiting examples of film-forming polymers include hydroxypropyl methylcellulose, hydroxypropyl cellulose, methylcellulose, polyvinyl pyrrolidine, and starches. Non-limiting examples of plasticizers include polyethylene glycol, tributyl citrate, dibutyl sebecate, castor oil, and acetylated monoglyceride. Furthermore, non-limiting examples of pigments and opacifiers include iron oxides of various colors, lake dyes of many colors, titanium dioxide, and the like.

Dosage

The selected dosage level can depend upon, for example, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved with an acceptable safety profile. It will be understood, however, that the specific dose level for any particular patient can depend upon a variety of factors including, for example, the genetic makeup, body weight, general health, diet, time and route of administration, combination with other drugs and the particular condition being treated, and its severity. For the treatment of insomnia, preferably one dose is administered prior to bedtime.

As used herein, the term "unit dosage form," refers to physically discrete units suitable as unitary dosages for human and animal subjects, each unit containing a predetermined quantity of doxepin calculated in an amount sufficient to produce the desired effect in association with a pharmaceutically acceptable excipient, carrier or vehicle. In some embodiments, the unit dosage form can be, for example, a pill, a tablet, a film coated tablet, capsule, a caplet, a gel cap, a pellet, a bead, or the like. In some embodiments, the unit dosage form can be a tablet. In some embodiments, the unit dosage form can be a film coated tablet. In some embodiments, the amount of doxepin in a unit dosage form can be about 0.5 mg to about 9 mg, or about 1 mg to about 9 mg, or about 1 mg to about 6 mg.

In some embodiments, daily dosages of low dose doxepin can be about 1, 2, 3, 4, 5, 6, 7, 8, or 9 milligrams. In one embodiment, an initial daily dosage of about 1 milligram can be given. If the desired improvement in sleep is not achieved, then the dosage can be incrementally increased until the desired effect is achieved or until a maximum desired dosage is reached which can be, for example, 2 milligrams, 3 milligrams, 4 milligrams, 5 milligrams or 6 milligrams. It should be noted that other dosages of doxepin can be used in the embodiments described herein. For example, the dosage can be about 0.1 to about 10 milligrams.

The term "low dose" can refer to a daily dose range of between about 0.01 and 9 milligrams, or to even lower doses. In some embodiments the preferable dosage of doxepin can be between about 0.1 milligram and 9 milligrams. Preferably, the dosage can be about 0.1 milligrams, about 0.2 milligrams, about 0.3 milligrams, about 0.5 milligrams, about 1 milligram, about 2 milligrams, about 3 milligrams, about 4 milligrams, about 5 milligrams, 6 milligrams, about 7 milligrams, about 8 milligrams, or about 9 milligrams.

It should be noted that in some embodiments the formulations and methods described herein can be applied to any dosage of doxepin, including higher doses used to treat depression and anxiety. As one example, the formulations and methods can be applied to dosages between about 10 milligrams and 20 milligrams or higher.

Methods of Making Compositions

The compositions described herein can be made by any suitable process, including any process that results in the a composition having one or more of the properties described herein. Several examples of processes and methods that can be used to make compositions are described herein.

Pharmaceutical preparations for oral use can be obtained by mixing one or more solid excipients with a pharmaceutical composition as described herein, optionally grinding the resulting mixture, and processing the mixture of granules, after adding suitable auxiliaries, if desired, to obtain tablets or dragee cores. In one embodiment, the compositions can be prepared using a dry granulation process. Alternatively, a wet granulation process can be used. In other embodiments, fluid bed granulation processing techniques are used.

One such granulation method is the "wet" granulation process, wherein dry solids (drug substance, filler, binder etc.) are blended and moistened with water or another wetting agent (e.g. an alcohol) and agglomerates or granules are built up of the moistened solids. Wet massing is continued until a desired homogenous particle size has been achieved whereupon the granulated product is dried. Some embodiments can include the use of wet granulation processes as part of the methods of making compositions.

In a preferred embodiment, the compositions disclosed herein can be prepared using direct compression. In another preferred embodiment, compressed tablets can be film coated. In some embodiments of the invention disclosed herein, the use of wet granulation techniques can be specifically excluded.

As used herein, "direct compression" means that the solid unit dosage form is prepared by compression of a simple mixture of the active pharmaceutical ingredient and excipients, without the active ingredient having been subjected to an intermediate granulation process in order to embed it in a larger particle and improve its fluidity properties.

In direct compression, the formulation ingredients, including the active pharmaceutical ingredient and processing aids, are incorporated into a free flowing blend. In one embodiment, the active ingredient, excipients, and other substances are blended and then compressed into tablets. Tablets are typically formed by pressure being applied to a material in a tablet press. Compressed tablets can be film coated.

Advantages of direct compression over wet and dry granulation processes, can include, for example, shorter processing times and cost advantages.

In one embodiment, a dry blend is used in forming low-dose doxepin or doxepin-related compound tablets, including film coated tablets, through gravity-fed, direct compression tableting. By "gravity fed tableting press" it is meant that a pharmaceutical formulation is not force fed into a die, and that the flow of the pharmaceutical formulation is induced by gravity. An example of a gravity fed tableting press is the Manesty F-press.

Preferably, the doxepin hydrochloride tablet products (including film coated and non-film coated tablets) disclosed herein are manufactured with common and simple processes including direct blending, compression and film-coating using commercially available pharmaceutical equipment. These operations utilize readily available equipment, do not expose the API to excessive moisture and heat, and are scalable. Preferably, the commercial manufacturing process produces and maintains blends and tablets with uniform potency that meet all quality characteristics. In a preferred embodiment, the manufacturing processes for all dosage strength formulations can be the same.

The manufacturing process can include the steps of: (1) preparing a color pre-blend; (2) preparing a drug substance pre-blend (also known as an active blend); (3) creating a main blend with all ingredients except magnesium stearate (lubricant); (4) adding lubricant and performing the final blend mixing step; (5) compressing the blend to produce tablets and (6) film-coating tablets. In some aspects, one or more of the above-listed steps can be excluded and the steps can be performed in any suitable order, not just the listed order.

The process can optionally include several techniques to facilitate formation of blends and batches of finished drug product with homogeneous distribution of drug substance and colorants including, for example: (1) de-agglomerating ingredients prior to blending; and/or (2) layering the drug substance and colorant components between additions of SMCC prior to mixing to create uniform pre-blends; and/or (3) serially diluting the drug substance and colorant pre-blends with SMCC and other formulation excipients to create uniform final blends. In addition, the process can optionally include, for example, (1) performing blend mixing time studies and assessing drug substance uniformity; and/or (2) optimizing the blend batch size with respect to the effective working capacity of the blenders.

Efficient mixing and acceptable blend and content uniformity are difficult to obtain for low dose dosage forms. Preferably, the choice of blenders and the configuration of the storage container to tablet press powder transfer chute are selected based on optimization and maintenance of content uniformity. In addition, excipients and process parameters can be selected to optimize main compression force and tablet press speed on the physical characteristics (hardness, friability, thickness and weight) of the finished dosage form.

In addition, the process can be optimized to compensate for the tendency for fluidization segregation of drug substance. For example, fluidization segregation can be reduced by eliminating process steps during which streams of air come in contact with the powder, for example, the step in the process when the blend is discharged from a V-blender into storage containers, and/or the step in the process when powder is fed from storage containers to the tablet press feed hopper.

In a preferred embodiment, the formulation is simple and contains few functional components. Thus, in one embodiment, SMCC can be the major excipient and no additional diluents, binders or disintegrants are used to achieve a readily compressible tablet formulation. In another embodiment, only one or two additional excipients are used.

Preferably, the formulation can have excellent compression and flow properties and the tablet press can be operated at very high press speeds and this allows relatively manageable tablet press run times for even large batch sizes.

In some embodiments, the direct compression manufacturing processes disclosed herein achieve a uniform drug product of a small unit dose of drug substance without the need for complex wet or dry granulation manufacturing techniques. In a preferred embodiment, the manufacturing process avoids costly techniques, such as those requiring large capital equipment investments, long manufacturing cycle times and associated low throughput.

In one embodiment, the manufacturing process is designed to achieve a uniform blend by using multiple blending steps, a specific order of addition in the blenders and screening steps to facilitate effective dispersion of the drug substance and excipients. For example, a screening step can be introduced to prevent agglomerates of drug substance from being carried over to subsequent manufacturing steps.

In another embodiment, the manufacturing process is designed to maintain the uniform blend through to tableting via minimizing the transfer steps, for example, by using an in-bin blender to form the final blend and for example via use of a vented and valved transfer chute to the tablet press.

Methods of Using Low Dose Doxepin

Some embodiments relate to methods for improving sleep in a patient in need thereof, for example by providing or administering low-dose doxepin, or a low-dose doxepin-related compound, in a tablet formulation (including coated tablet formulations) as described herein. The term "administer" and its variants contemplate both self-administration (by the patient) and administration by a third party. In a preferred embodiment, the oral pharmaceutical SMCC-containing doxepin formulations described herein are administered orally.

As mentioned above and elsewhere, the methods described herein can be used to treat individuals suffering from a sleep disorder, such as insomnia. The individual can suffer from a chronic insomnia or a non-chronic insomnia. For chronic (e.g., greater than 3-4 weeks) or non-chronic insomnias, a patient may suffer from difficulties in sleep onset, sleep maintenance (interruption of sleep during the night by periods of wakefulness), sleep duration, sleep efficiency, premature early-morning awakening, or a combination thereof. Also, the insomnia may be attributable to the concurrent use of other medication, for example. The non-chronic insomnia can be, for example, a short term insomnia or a transient insomnia. The chronic or non-chronic insomnia can be a primary insomnia or an insomnia that is secondary or attributable to another condition, for example a disease such as depression or chronic fatigue syndrome. In some aspects, the patient can be one that is not suffering from an insomnia that is a component of a disease, or a patient can be treated that is otherwise healthy. As previously mentioned, the chronic or non-chronic insomnia can be a primary insomnia, that is, one that is not attributable to another mental disorder, a general medical condition, or a substance. In many cases, such conditions may be associated with a chronic insomnia and can include, but are not limited to, insomnia attributable to a diagnosable DSM-IV disorder, a disorder such as anxiety or depression, or a disturbance of the physiological sleep-wake system. In some aspects the insomnia can be non-chronic, or of short duration (e.g., less than 3-4 weeks). Examples of causes of such insomnia may be extrinsic or intrinsic and include, but are not limited to environmental sleep disorders as defined by the International Classification of Sleep Disorders (ICSD) such as inadequate sleep hygiene, altitude insomnia or adjustment sleep disorder (e.g., bereavement). Also, short-term insomnia may also be caused by disturbances such as shift-work sleep disorder.

It should be noted that in some aspects, the methods can specifically exclude one or more of any of the sleep disorders described in the previous paragraph or elsewhere herein. For example, without being limited thereto, in some aspects the methods can specifically exclude treating a chronic insomnia. As another example, without being limited thereto, in some aspects the methods can specifically exclude treating an insomnia that is attributable to a condition such as depression, anxiety or chronic fatigue.

In a preferred embodiment, the methods can include treating onset, duration, and maintenance aspects of insomnia in a patient.

The pharmaceutical tablet formulations (including coated tablets) disclosed herein have surprising efficacy, even in low doses, and also can allow a full 7 or 8 hours of sleep, or more, without significant next-day sedation. It is believed that these formulations are safe, provide rapid sleep onset, maintains sleep throughout the night for a full 7 or 8 hour sleep cycle, and allow normal activity the next day without hangover or unsafe levels of sedation.

EXAMPLES

Several of the examples below describe multiple strengths (1 mg, 3 mg and 6 mg) of a stable, immediate-release, solid, oral dosage. Tablet formulations were developed after extensive testing and development, and after overcoming several previously unmet and unexpected challenges.

Example 1

1 mg, 3 mg, and 6 mg Formulations

Examples of 1 mg, 3 mg, and 6 mg formulations are provided in Table 1 and Table 2.

TABLE 1

| | | Non-film coated tablets | | | | | |
|---|---|---|---|---|---|---|---|
| | | 1 mg | | 3 mg | | 6 mg | |
| Item | Material | % | Mg/tab | % | Mg/tab | % | Mg/tab |
| 1 | Doxepin HCl | 0.753 | 1.13 | 2.26 | 3.39 | 4.52 | 6.78 |
| 2 | Silicified Microcrystalline Cellulose | 98.53 | 147.80 | 96.71 | 145.07 | 94.00 | 141.00 |

TABLE 1-continued

| | | Non-film coated tablets | | | | | |
|---|---|---|---|---|---|---|---|
| | | 1 mg | | 3 mg | | 6 mg | |
| Item | Material | % | Mg/tab | % | Mg/tab | % | Mg/tab |
| 3 | Colloidal Silicon Dioxide | 0.16 | 0.24 | 0.47 | 0.71 | 0.88 | 1.32 |
| 4 | FD&C Blue 1 Al Lake 10-13% | - - - | - - - | 0.05 | 0.08 | 0.02 | 0.03 |
| 5 | DC Yellow 10 Al Lake 36-42% | 0.04 | 0.06 | - - - | - - - | 0.08 | 0.12 |
| 6 | FD&C Yellow #6 Al Lake 15-18% | 0.01 | 0.015 | - - - | - - - | - - - | - - - |
| 7 | Magnesium Stearate | 0.50 | 0.75 | 0.50 | 0.75 | 0.50 | 0.75 |
| | Totals: | 100.00 | 150.00 | 100.00 | 150.00 | 100.00 | 150.00 |

TABLE 2

| | | Film-coated tablets | | | | | |
|---|---|---|---|---|---|---|---|
| | | 1 mg | | 3 mg | | 6 mg | |
| Item | Material | % | Mg/tab | % | Mg/tab | % | Mg/tab |
| 1 | Doxepin HCl | 0.724 | 1.13 | 2.17 | 3.39 | 4.35 | 6.78 |
| 2 | Silicified Microcrystalline Cellulose | 94.79 | 147.88 | 93.04 | 145.15 | 90.48 | 141.15 |
| 3 | Colloidal Silicon Dioxide | 0.15 | 0.24 | 0.46 | 0.71 | 0.85 | 1.32 |
| 4 | Magnesium Stearate | 0.48 | 0.75 | 0.48 | 0.75 | 0.48 | 0.75 |
| 5 | Film coat | 3.8 | 6 | 3.8 | 6 | 3.8 | 6 |
| | Totals | 100.00 | 156.00 | 100.00 | 156.00 | 100.00 | 156.00 |

Example 2

Doxepin Multimedia Dissolution Study

The dissolution of 1 mg (Lot Number 3047751R) and 6 mg (Lot Number 3047758R) SMCC-formulated, doxepin tablets in Simulated Gastric Fluid without enzymes (pH 1.2), 0.05 M acetate buffer (pH 4.5) and Simulated Intestinal Fluid USP without enzymes (pH 6.8) was measured with USP Apparatus 2 at 50 rpm using 900 mL of 37° C.±0.5° C. dissolution media at 3, 5, 10, 15 and 30 minute time points. The average (n=12 tablets) percent doxepin released for each dosage strength in the two media at each time point is reported in Table 3.

TABLE 3

| | Simulated Gastric Fluid (pH 1.2) | | 0.05M Acetate Buffer (pH 4.5) | | Simulated Intestinal Fluid (pH 6.8) | |
|---|---|---|---|---|---|---|
| Time point | 1 mg | 6 mg | 1 mg | 6 mg | 1 mg | 6 mg |
| 3 minutes | *83% | 70% | *84% | 71% | 55% | 57% |
| 5 minutes | *91% | *85% | *93% | *80% | 69% | 72% |
| 10 minutes | *94% | *90% | *99% | *91% | 79% | *81% |
| 15 minutes | *96% | *94% | *101% | *95% | *81% | *84% |
| 30 minutes | *97% | *97% | *102% | *98% | *86% | *87% |

The conditions with an asterisk in Table 2 achieve a Q value of 80% with none of the individual dissolution values falling below Q—15%.

Example 3

Comparative Dissolution

Table 4 contains comparative dissolution data generated for commercially-available, high-dose doxepin (i.e. 50 mg and 75 mg Sinequan) as well as lactose and SMCC-based, low-dose doxepin formulations. The reported data are an average of a least 6 dissolution values for the various formulations at the indicated time points and were generated using the USP-based method, which methods are incorporated herein by reference in their entireties, for measurement of doxepin dissolution. These data clearly show that the low-dose doxepin formulations exhibit significantly faster dissolution characteristics.

TABLE 4

| | Dissolution | | | | |
|---|---|---|---|---|---|
| | Percent (%) Released | | | | |
| Elapsed Time (minutes) | Sinequan (50 mg) | Sinequan (75 mg) | Low Dose Doxepin Capsule (lactose) | Low Dose Doxepin Tablet— Uncoated (SMCC) | Low Dose Doxepin Tablet— Coated (SMCC) |
| 0 | 0 | 0 | 0 | 0 | 0 |
| 3 | NT[a] | NT | NT | 75.3 | 63.1 |
| 5 | 6 | 16 | 92.1 | 94.3 | 81.8 |
| 8 | NT | NT | 91.8 | NT | NT |

TABLE 4-continued

| | | | Dissolution | | |
|---|---|---|---|---|---|
| | | | Percent (%) Released | | |
| Elapsed Time (minutes) | Sinequan (50 mg) | Sinequan (75 mg) | Low Dose Doxepin Capsule (lactose) | Low Dose Doxepin Tablet— Uncoated (SMCC) | Low Dose Doxepin Tablet— Coated (SMCC) |
| 10 | 40 | 38 | ND | 96.9 | 91.6 |
| 12 | NT | NT | 92.9 | NT | NT |
| 15 | 70 | 62 | 93.6 | 97.9 | 94.1 |
| 30 | 101 | 96 | 89.9 | 99.1 | 97 |

<sup>a</sup>NT = "Not tested" at that time point for that formulation

Thus, some embodiments relate to low dose doxepin formulations that have the unexpected dissolution properties listed above. For example, some embodiments relate to formulations that release at least from about 60% to about 99.5% doxepin after about 5 to about 40 minutes. The release or dissolution can be determined using the USP-based methods. Preferably, 60%, 65%, 70%, 75%, 80%, 85%, 90%, 95% or 99.5% doxepin is released after 3, 5, 10, 15 or 30 minutes, for example.

Example 4

Blend Uniformity

Due to the very low concentrations of drug substance in these tablet formulations, the blending process included preparation of a drug substance pre-blend created by layering doxepin HCl between additions of SMCC, followed by mixing. The uniformity of unit dose potency was further promoted by serially diluting and mixing the drug substance pre-blend with the remaining SMCC and colloidal silicon dioxide. FIG. 1 graphically illustrates the preparation of a drug substance pre-blend, which can result in the uniform distribution of drug substance in the drug product.

Thus, some embodiments relate to methods of improving blend uniformity, for example, by layering low dose doxepin with a filler, such as SMCC. It should be noted that other fillers can be used rather than SMCC or in addition to SMCC. Furthermore, uniformity can be improved by serially diluting the mixtures as described above with SMCC or any other filler or combination of fillers.

Example 5

Content Uniformity—Fluidized Segregation

Following the production of 10 kg batches for clinical evaluation, the drug product manufacturing process was scaled up to 120 kg and the final formulation (colored tablets) was manufactured. Evaluation of content uniformity data associated with tablets compressed from these 120 kg batches demonstrated lower than expected assay values for tablets produced at the beginning of the tablet compression operation and higher than expected assay values for tablets produced at the end of the compression operation. Fluidization segregation was determined to be responsible for this content uniformity variability.

In order to avoid fluidization segregation, process steps that allow streams of air to come in contact with free falling powder were eliminated. Thus, in some embodiments, the process steps can include reducing the contact of streams of air with the free falling powder and/or any other fluidization segregation reduction method.

In scaling up the process to 560 kg, the following process and equipment changes were implemented to optimize tablet content uniformity. The changes are not meant to limit the manner in which the formulations can be produced or to be construed as teaching away from the uses of certain apparatus or to exclude the use of certain of the changed apparatus. In fact, the changed apparatus and/or methods can be utilized in some aspects alone or in any combination. The changes are provided to show several preferred aspects of the embodiments.

Change 1: Use a 5 ft$^3$ V-blender rather than a 3 ft$^3$ cross-flow blender for the preparation of the active pre-blend and a 60 ft$^3$ in-bin blender rather than a 10 ft$^3$ V-blender for final blend to assure that the volume of powder in the blenders does not exceed the effective working volume of tumble blenders.

Change 2: Store final blend in the 60 ft$^3$ in-bin blender rather than discharge from V-blender into storage containers in order to eliminate a process step that can cause fluidization segregation.

Change 3: Addition of valves and vents to the powder transfer chute through which blend is delivered to the tablet press from the blend storage container. A multi-segment transfer chute equipped with a series of valves that are sequentially opened allows the gradual introduction of blend into the tablet press feed frame rather than blend free-falling from the blend storage vessel through the current single-piece chute. The presence of filter-equipped vents on the multi-segment powder transfer chute allows air, displaced when a segment of the powder transfer chute fills with powder, to escape through a vent rather than the displaced air being forced through the blend in the bin. This eliminates another potential source of drug substance fluidization segregation.

Figure 2:
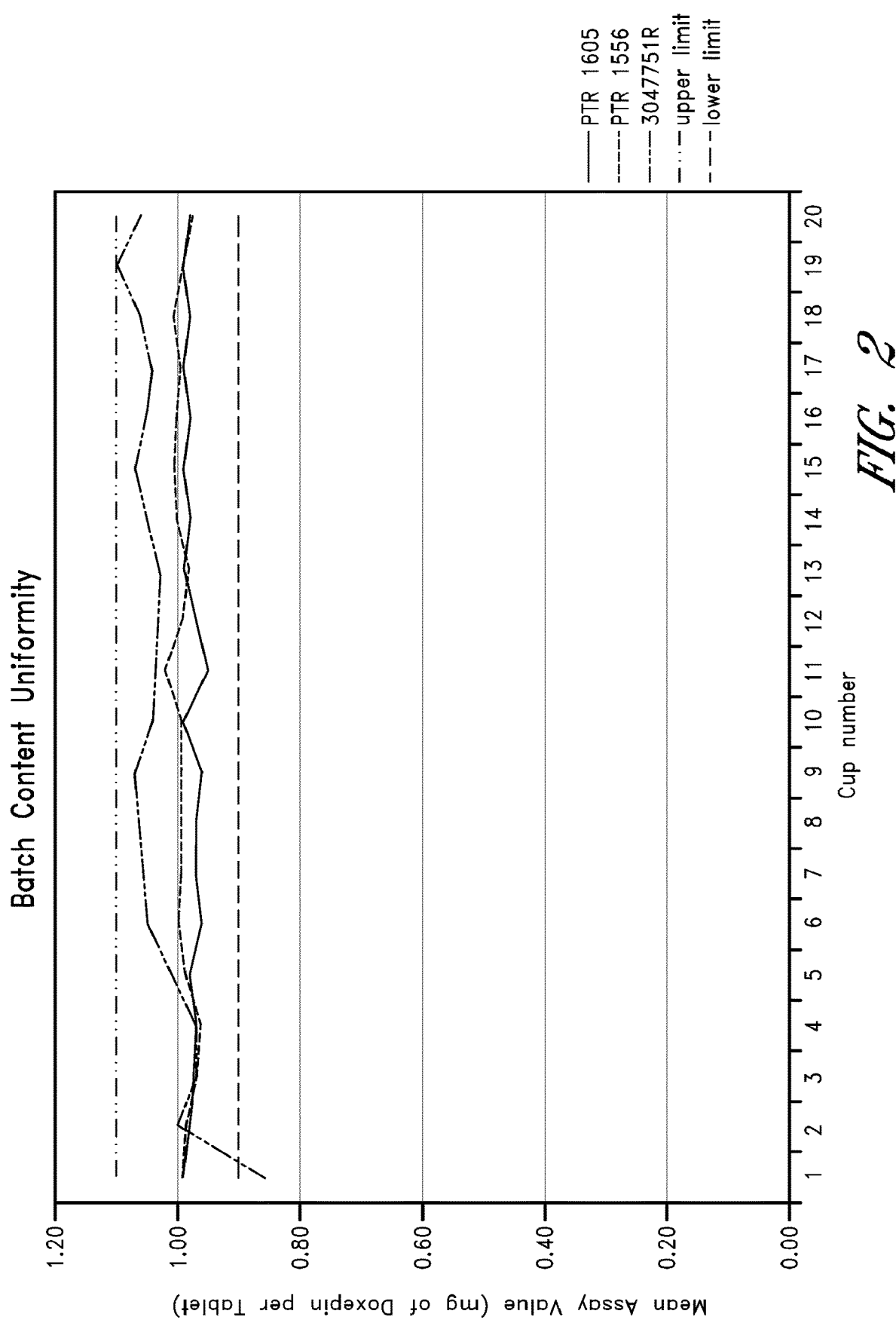
FIG. 2 is a graph showing a batch content uniformity comparison.

To confirm that the foregoing process changes resulted in better content uniformity, two feasibility batches were produced at approximately commercial scale. Both batches were formulated at a theoretical potency of 1 mg since that dosage strength exhibited content uniformity values greater than 10% from target at both the beginning and end of the compression operation. To facilitate uniform dispersal of drug substance in the formulation, the strategies of layering doxepin HCl, USP between additions of SMCC to create a drug substance pre-blend and taking opportunities to serially dilute the drug substance pre-blend with additional SMCC were incorporated into the scaled-up manufacturing process. FIG. 2 presents a graphical comparison of content uniformity associated with tablets systematically sampled throughout the 120 kg registration stability batch (3047751R) and the feasibility batches at commercial scale (PTR 1556 and 1605).

Briefly, low-dose doxepin tablets were manufactured at a scale of 560 kg by standard processes which included dry blending, direct compression and primary packaging into high density polyethylene bottles with polypropylene child-resistant closures and pharmaceutical cotton for void fill (HDPE bottles) as well as polyvinyl chloride/polyvinylidene chloride (PVC/PVDC), heat-sealed foil-laminate blister strips (blisters) using commonly available pharmaceutical equipment.

Thus, some embodiments relate to methods of improving uniformity by minimizing segregation, including fluidized segregation. The methods can include one or more of utilizing devices with vents, valves or other mechanisms that permit the escape of air or that minimize the contact of air with the low dose doxepin blends, for example.

Example 6

Content Uniformity—API Agglomeration

Low dose doxepin tablets can exhibit potencies outside the USP range that constitutes uniformity of dosage units. This can be caused by non-uniform distribution of drug substance in the formulation. This can be due, for example, to small agglomerates of drug substance present in the final blend following the series of operational steps associated with the blend manufacturing process. A technical investigation unexpectedly confirmed that drug substance was re-agglomerating following operational steps that allowed screened particles of cohesive powders to re-associate. For instance, when particles of insufficiently-diluted drug substance pass through the screen on a SWECO-type vibratory sieve, they fall onto a shelf below the screen. The circular, vibrating motion of the sieve can cause re-agglomeration of drug substance as the screened particles physically interact during their mechanically-induced migration to the discharge orifice of the vibratory sieve. To avoid drug substance re-agglomeration, portions of drug substance were layered between larger portions of SMCC and mixed to adequately dilute the drug substance. The diluted and mixed drug substance pre-blend was then screened using a cone-mill that eliminates situations in which inadequately diluted portions of drug substance were screened in a manner that allowed re-agglomeration.

Thus, some embodiments relate to methods of preventing, avoiding or minimizing re-agglomeration low dose doxepin mixtures or formulations. Such methods can include diluting the drug substance, for example, as described above by layering the drug substance between larger portions of SMCC. Any other suitable method can also be used which dilutes the drug substance and/or which minimizes re-agglomeration. Also, the methods can include the use of a cone mill, a co mill or any other like device.

Example 9

Large Scale Manufacturing Process for Non-Film Coated Tablets

Figures 1, 3:
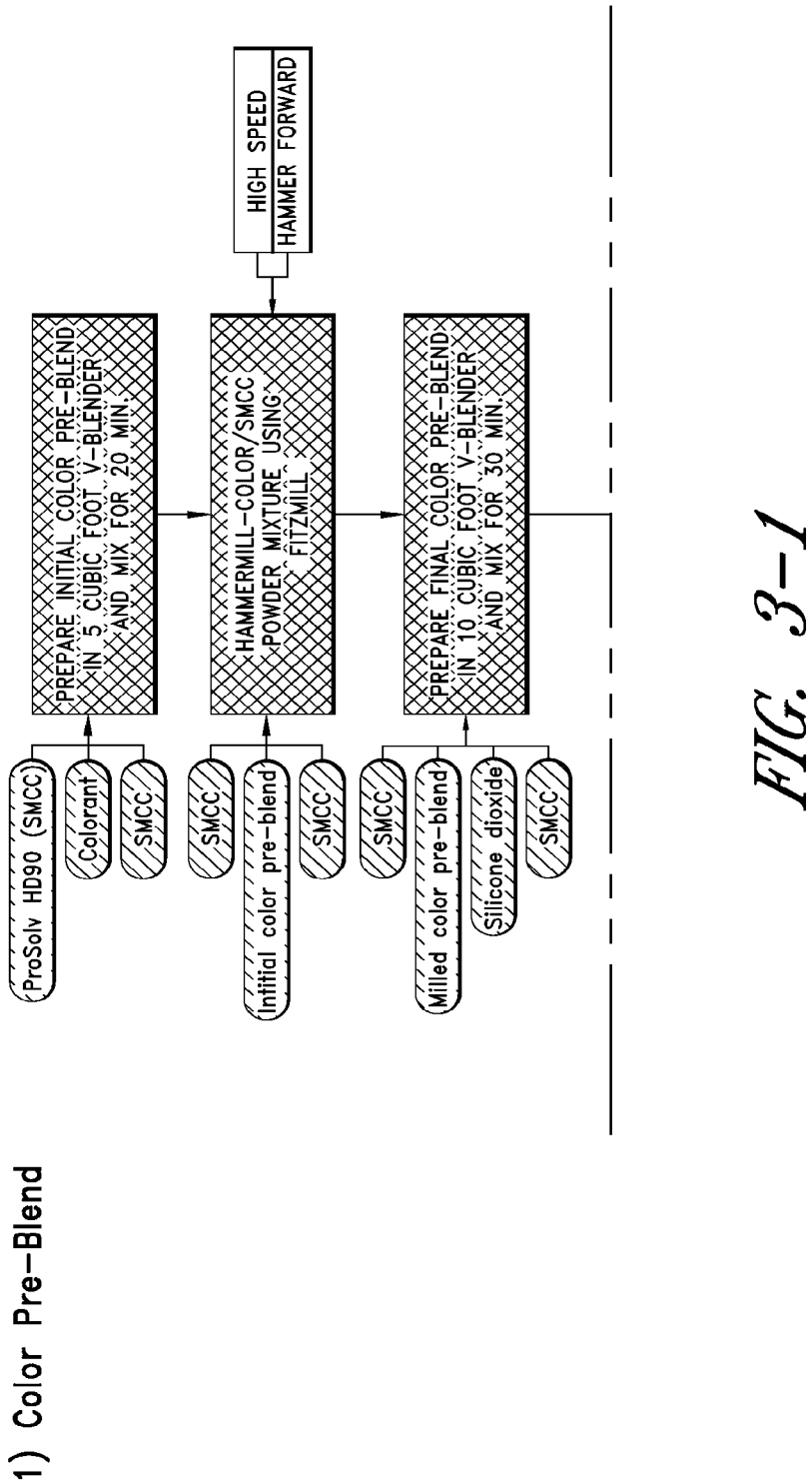
FIG. 3 is a flow chart showing an exemplary manufacturing process.
Figures 2, 3:
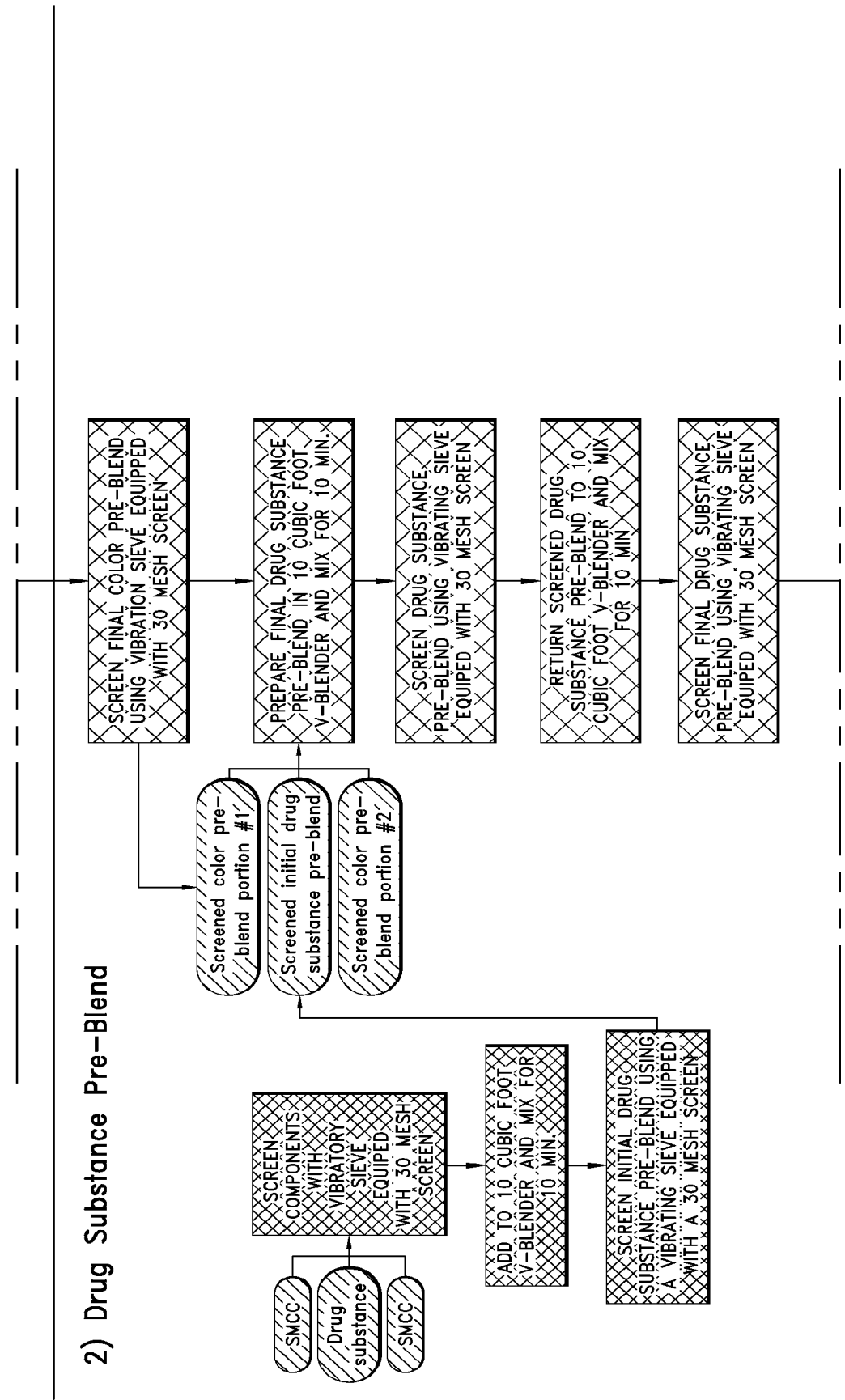
Figure 3:
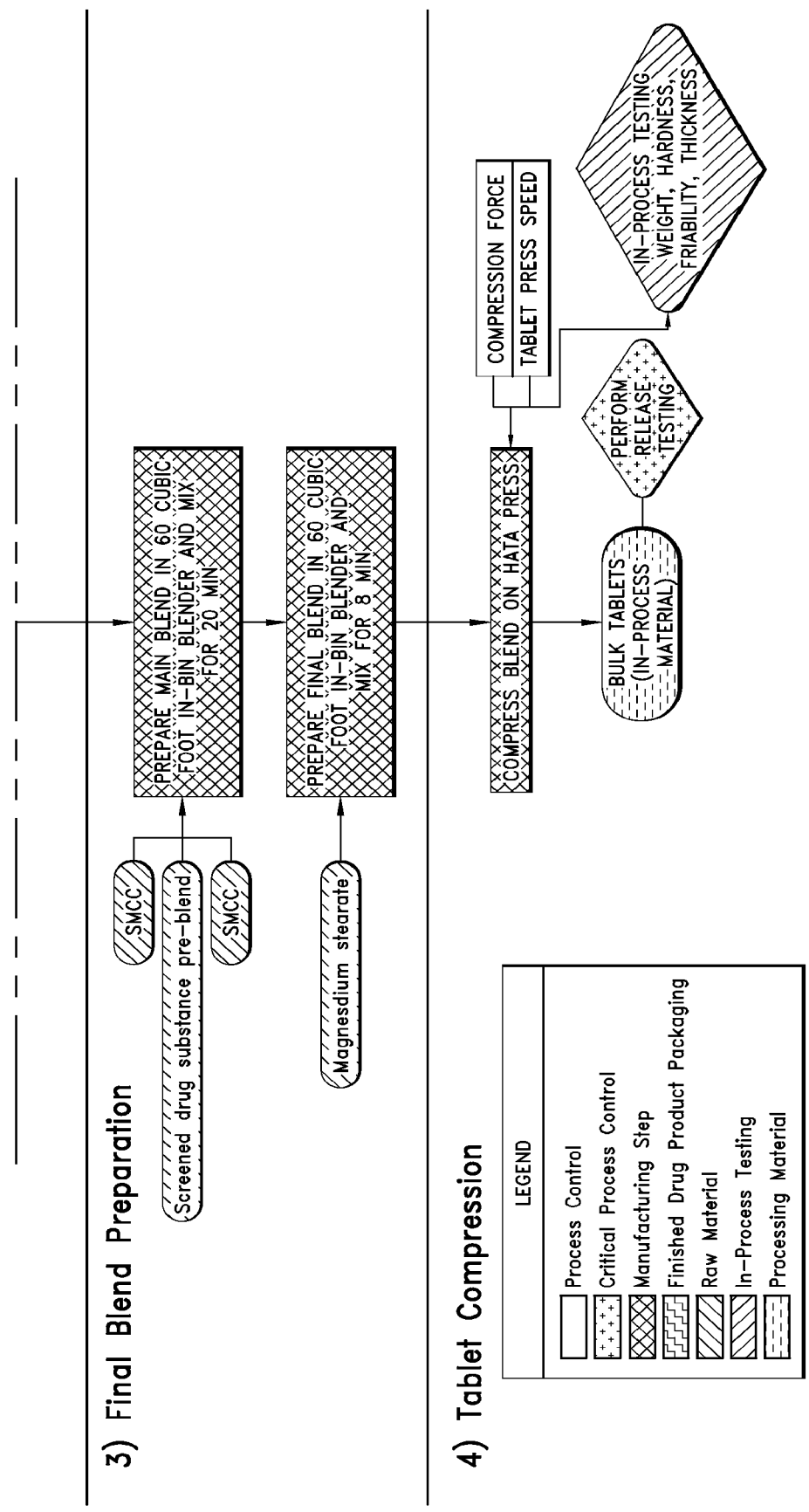

The following manufacturing process description is for the 3 mg formulation at a 560 kg batch size and is relevant for the other low-dose tablet formulations. FIG. 3 provides a summary of the process described below. The batch size is representative of potential commercial batch sizes and is not intended to limit the invention. One skilled in the art would appreciate that the batch size is arbitrary and a range of batch sizes are encompassed by this invention.

Figure 4:
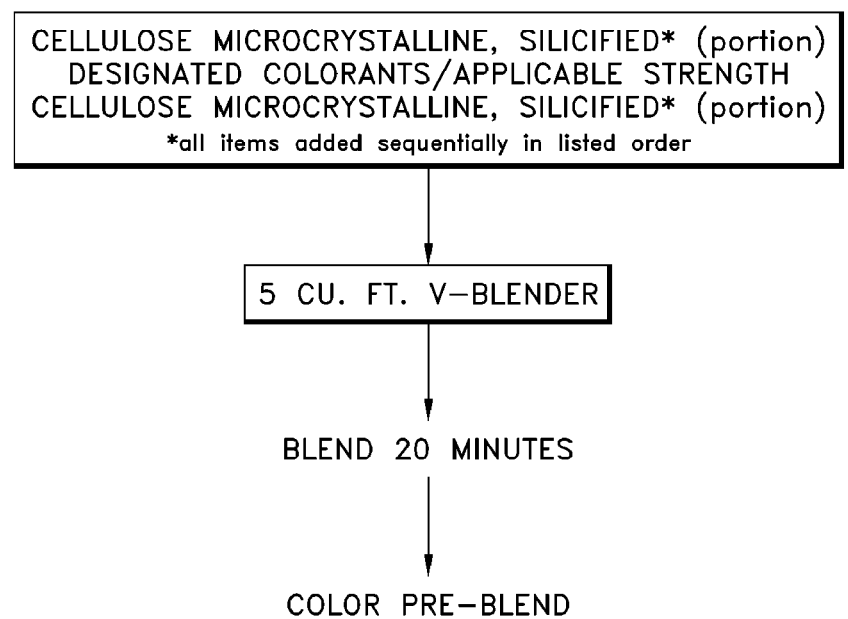
FIGS. 4-6 are flow charts showing preparation of a color pre-blend.
Figure 5:
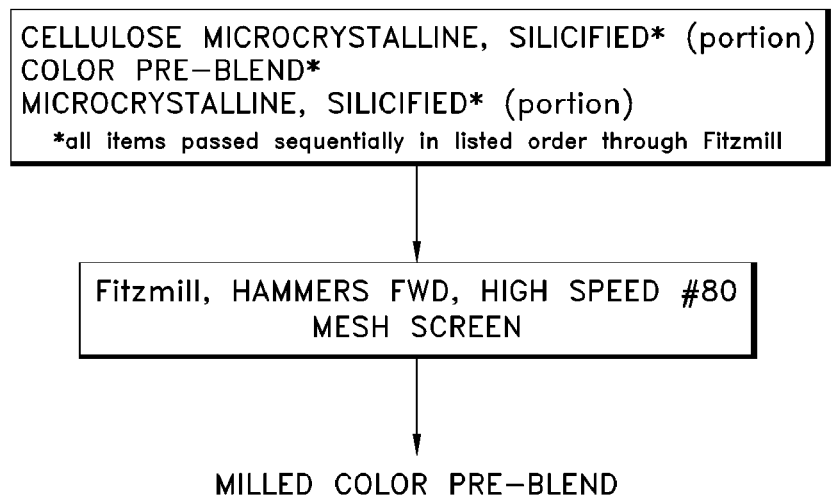
Figure 6:
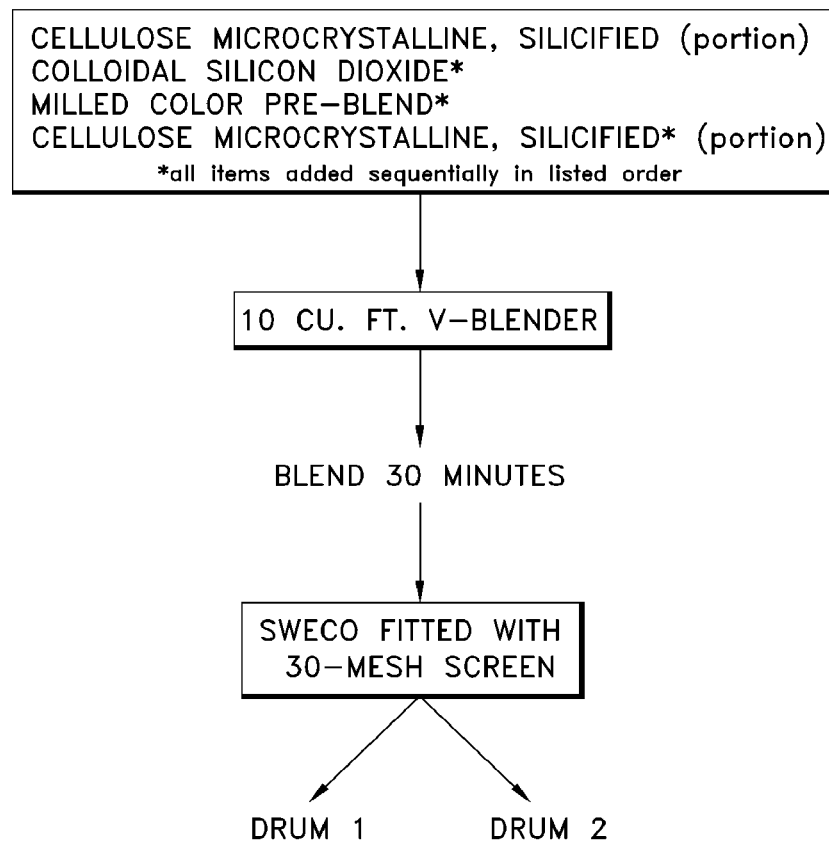

Color Pre-blend (FIGS. 4-6)

A color pre-blend was prepared by a three step blend-mill-blend process. Approximately 5% (25.7 kg) of SMCC, the entire quantity of colorant and another approximately 5% of SMCC were sequentially added to a 5 cubic foot V-blender and mixed for 20 minutes. Then, this blend was processed in a hammer mill equipped with an 80 mesh screen at high speed with the hammers forward. Prior to hammer milling the color pre-blend, a 2 kg portion of SMCC was processed. This allowed layering of the milled color pre-blend between layers of SMCC following the dry rinsing of the hammer mill with another 2 kg portion of SMCC. Lastly, the hammer-milled color pre-blend was added to a 10 cubic V-blender containing 21 kg of SMCC. 2.63 kg colloidal silicon dioxide was added to the V-blender followed by another 21 kg of SMCC to again layer and serially-dilute the color component. The powder mixture was mixed for 30 minutes and discharged directly through a vibrating sieve equipped with a 30 mesh screen into two separate drums.

The approximately equal quantities of color pre-blend in the two drums were used to layer the drug substance in the next phase of the manufacturing process.

Figure 7:
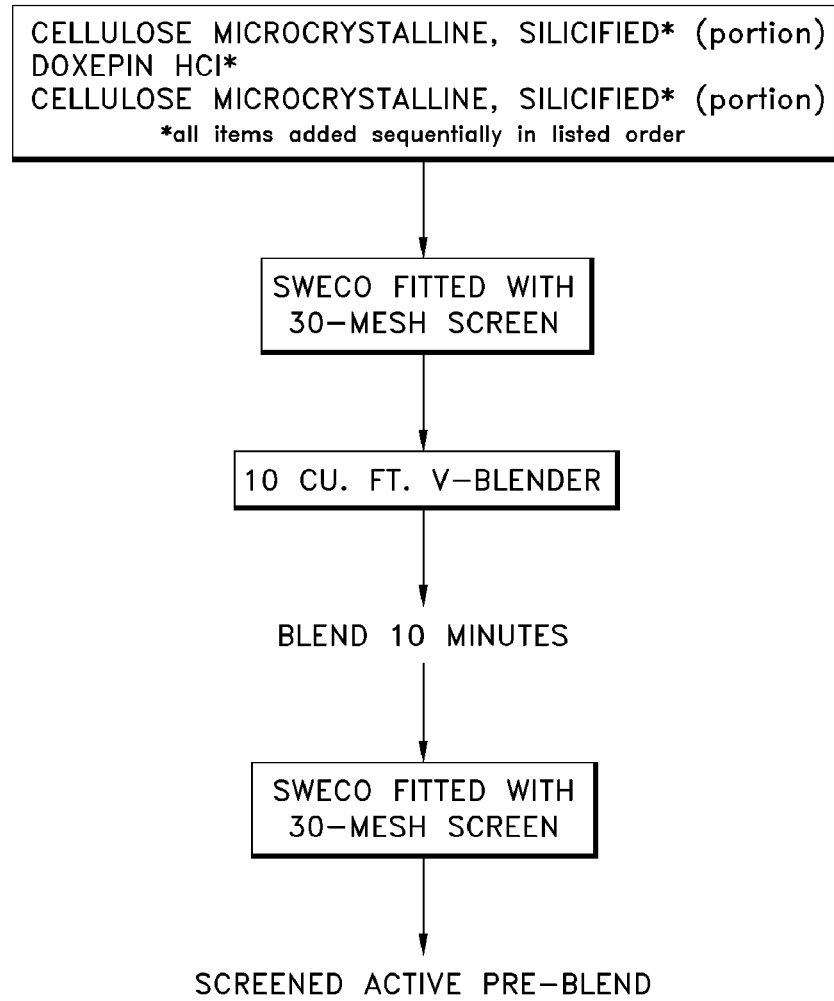
FIGS. 7-8 are flow charts showing preparation of a drug substance pre-blend.
Figure 8:
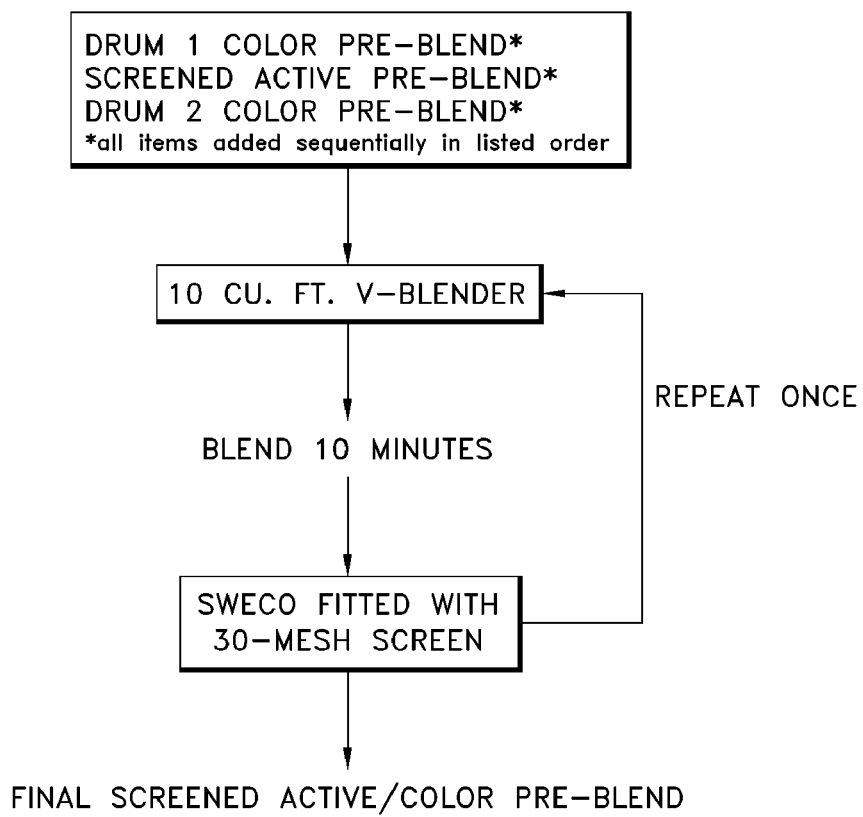

Drug Substance Pre-blend (FIGS. 7 and 8)

Next, the drug substance was de-agglomerated. Briefly, the entire quantity, 12.65 Kg, of doxepin hydrochloride was screened through the vibrating sieve equipped with a 30 mesh screen into an appropriate polyethylene-lined vessel containing 2 kg of SMCC. A small portion of SMCC was used to dry rinse the bag into which the drug substance was initially dispensed. This portion of SMCC was then passed through the vibrating sieve followed by a 20 kg portion of SMCC to dry rinse the 30-mesh screen.

The de-agglomerated drug substance and SMCC were added to the 10 cubic V-blender and mixed for 10 minutes. The initial drug substance was discharged and screened using a vibrating sieve equipped with a 30 mesh screen. The screened initial drug substance pre-blend was added to a 10 cubic foot V-blender containing one drum of screened color pre-blend. The second drum of screened color pre-blend was then added to the 10 cubic V-blender to layer the drug substance. A portion of the powder from the second drum was used to dry rinse the polyethylene bag, into which the drug substance was screened, and added to the V-blender. The material was mixed for 10 minutes and then discharged directly through the vibrating sieve equipped with a 30 mesh screen into polyethylene lined containers. The screened drug substance pre-blend was returned to the 10 cubic foot V-blender and mixed for an additional 10 minutes. The drug substance pre-blend was discharged directly through a vibrating sieve equipped with a 30-mesh screen into poly-lined containers.

In another embodiment, the doxepin hydrochloride drug substance can be milled using a pharmaceutically acceptable mill such as a fluid energy, impact, cutting, compression, screening or tumbling mill as defined in the Guidance for Industry SUPAC-IR/MR: Immediate Release and Modified Release Solid Oral Dosage Forms—Manufacturing Equipment Addendum, January 1999. This blending process step can use milled or de-agglomerated drug substance, for example.

Figure 9:
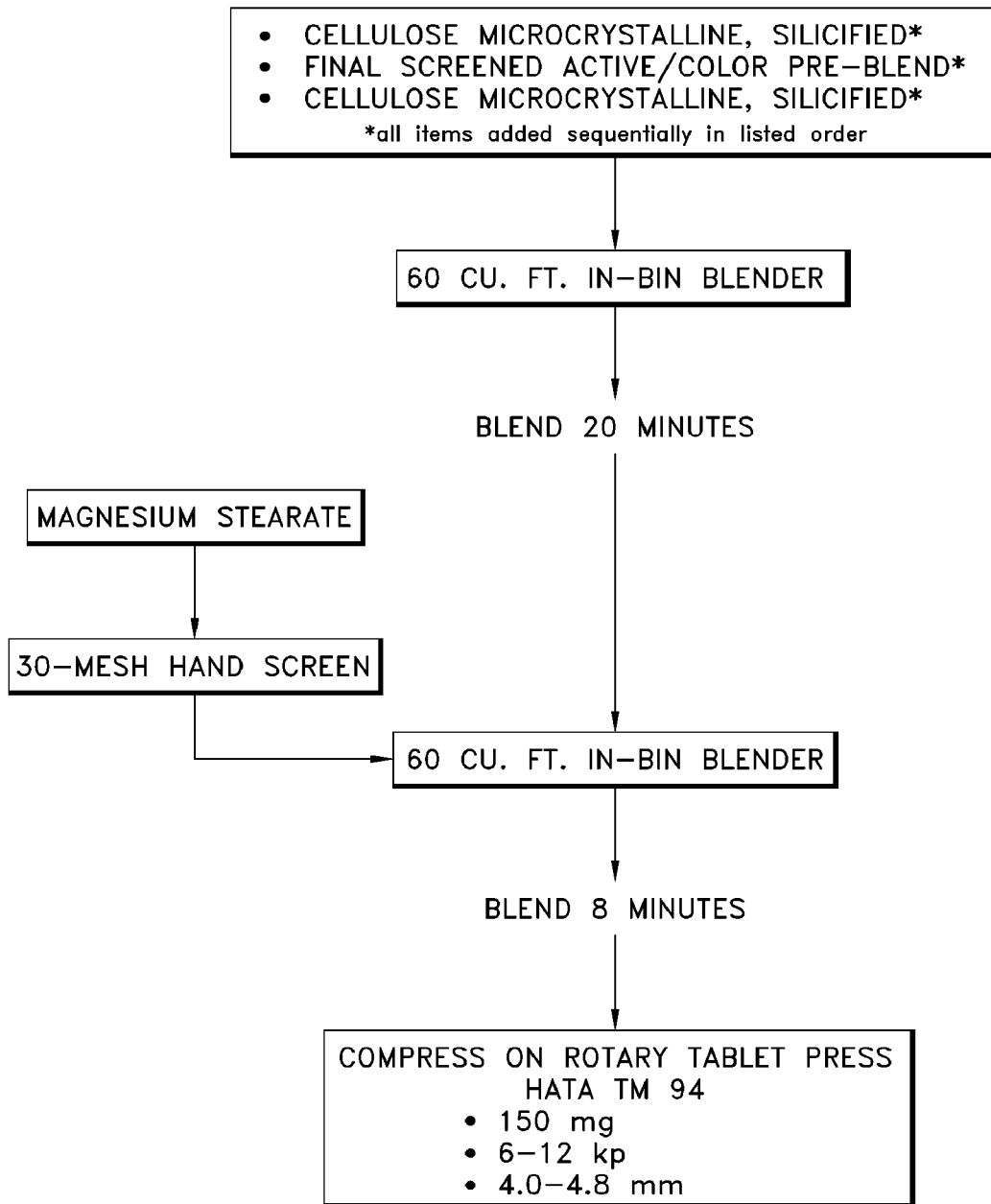
FIG. 9 is a flow chart showing preparation of a final blend.

Preparation of the Final Blend (FIG. 9)

The final blend was prepared by adding the screened drug substance pre-blend to a 60 cubic foot in-bin tumble blender containing 212 kg of SMCC. Another 212 kg of SMCC was then added to the 60 cubic foot in-bin tumble blender to layer and serially dilute the drug substance pre-blend. The material was mixed for 20 minutes.

Optionally, magnesium stearate, 2.8 kg, was then added to the 60 cubic foot in-bin tumble blender and mixed for 8 minutes. The blend was stored in the in-bin tumble blender until compressed into tablets.

Tablet Compression (FIG. 9)

Tablets were manufactured by positioning the final blend contained in the in-bin blender tote above the tablet press feed hopper. A segmented powder transfer chute was used to introduce doxepin powder mixtures into the press hopper with each segment of the powder transfer chute being equipped with a valve and a vent. The valves on the in-bin blender tote and each segment of the powder transfer chute were opened sequentially to reduce the volume of air that comes into contact with free-falling powder and to prevent fluidization segregation. Tablets were compressed on a single-sided, 38-station rotary HATA tablet press at a target speed of 35 to 70 rpm and main compression force of approximately 0.30 metric tons.

Example 8

Large Scale Manufacturing Process for Film-Coated Tablets

The following manufacturing process description is for a 3 mg formulation and can be used for other low-dose tablet formulations. The batch size is representative of potential commercial batch sizes and is not intended to limit the invention. One skilled in the art will appreciate that the batch size is arbitrary and a range of batch sizes are encompassed by this invention.

Figure 14:
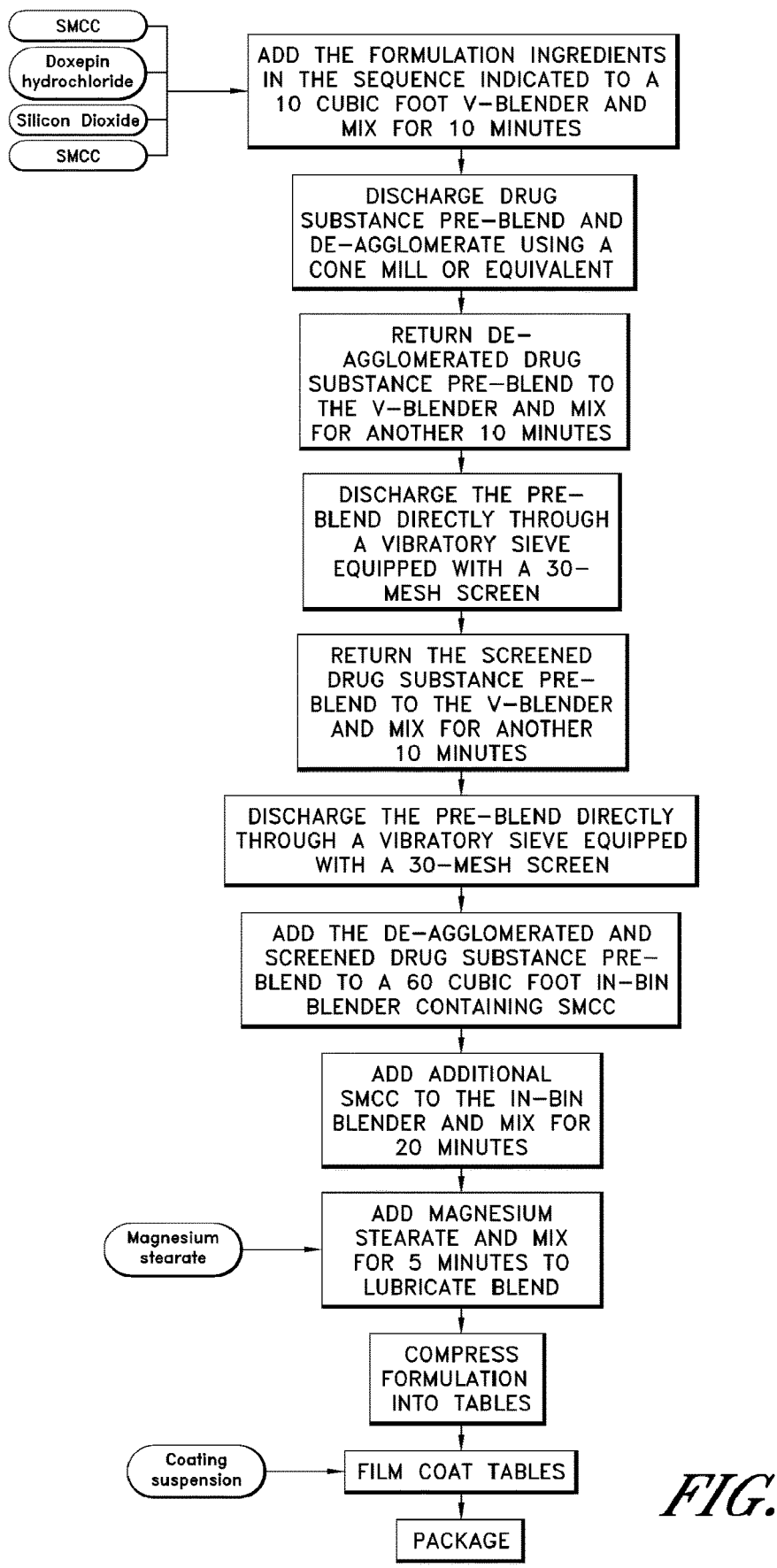
FIG. 14 is a manufacturing process flow chart depicting an example of a process for film-coated tablets.
Figure 15:
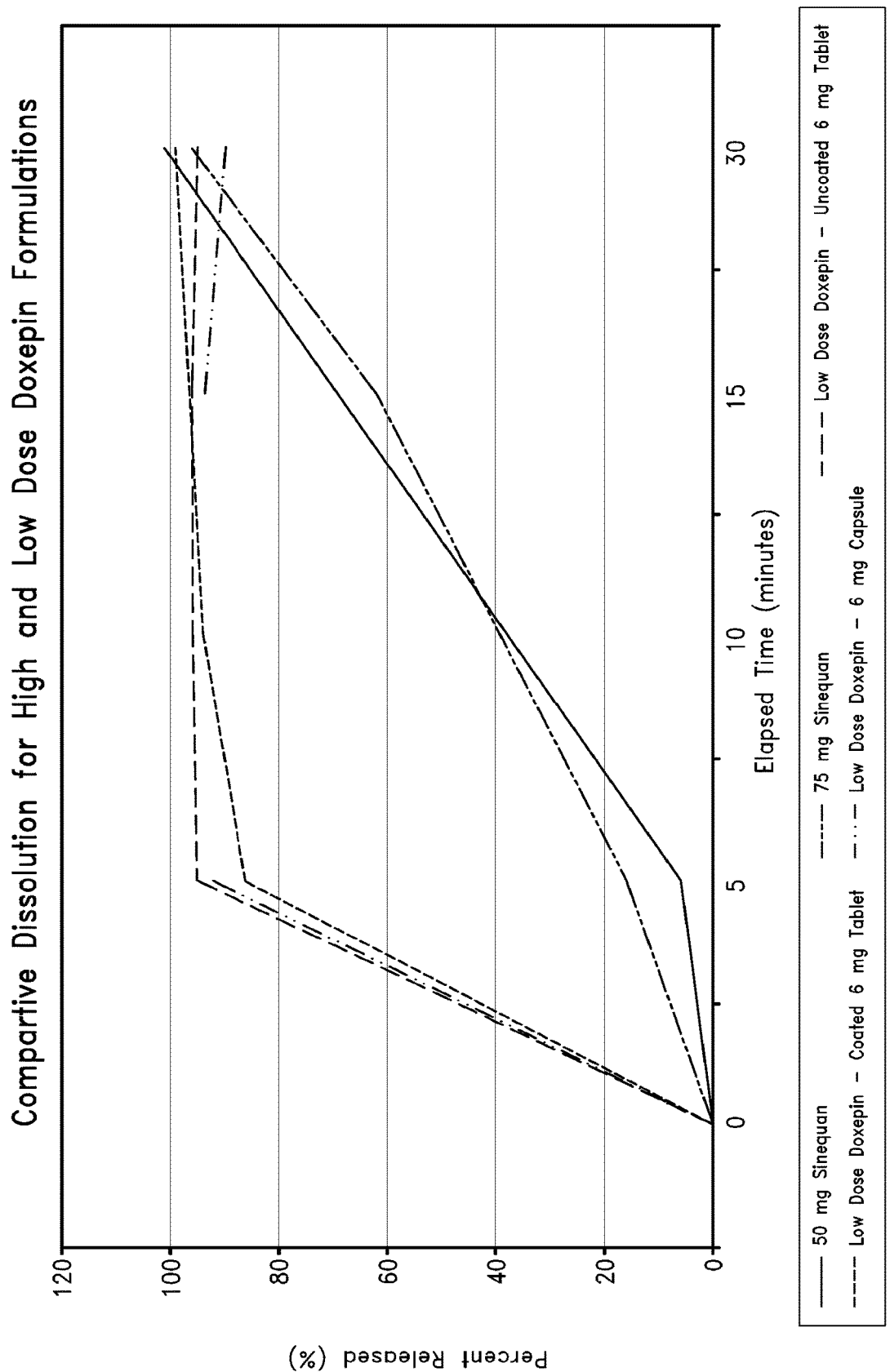
FIG. 15 is a graph of the dissolution data for commercially-available, high-dose doxepin formulations as well as lactose and SMCC-based formulations of low-dose doxepin.

Drug Substance Pre-blend (FIGS. 14 and 15)

Briefly, 12.66 Kg, of doxepin hydrochloride and 2.65 Kg of silicon dioxide are added to a ten cubic foot V-blender containing 55.93 Kg of SMCC. Another 55.93 Kg of SMCC are added to the blender and mixed for approximately 10 minutes. The discharged drug substance pre-blend is deagglomerated through a cone mill equipped with a 0.8 mm screen. The screened drug substance pre-blend is returned to the ten cubic foot V-blender and mixed for another 10 minutes. The drug substance pre-blend is discharged directly through a vibratory sieve equipped with a 30-mesh screen. The drug substance pre-blend is again returned to the V-blender, mixed for another 10 minutes and screened using a vibratory sieve equipped with a 30-mesh screen.

In another embodiment, the doxepin hydrochloride drug substance can be milled using a pharmaceutically acceptable mill such as a fluid energy, impact, cutting, compression, screening or tumbling mill as defined in the Guidance for Industry SUPAC-IR/MR: Immediate Release and Modified Release Solid Oral Dosage Forms—Manufacturing Equipment Addendum, January 1999, which is incorporated herein by reference in its entirety. This blending process step can use milled or de-agglomerated drug substance, for example.

Preparation of the Final Blend (FIG. 9)

The final blend was prepared by adding the screened drug substance pre-blend to a 60 cubic foot in-bin tumble blender containing 215 kg of SMCC. Another 215 kg of SMCC was then added to the 60 cubic foot in-bin tumble blender to layer and serially dilute the drug substance pre-blend. The material was mixed for 20 minutes.

Optionally, magnesium stearate, 2.8 kg, was then added to the 60 cubic foot in-bin tumble blender and mixed for 5 minutes. The blend was stored in the in-bin tumble blender until compressed into tablets.

Tablet Compression (FIG. 9)

Tablets were manufactured by positioning the final blend contained in the in-bin blender tote above the tablet press feed hopper. A segmented powder transfer chute was used to introduce doxepin powder mixtures into the press hopper with each segment of the powder transfer chute being equipped with a valve and a vent. The valves on the in-bin blender tote and each segment of the powder transfer chute were opened sequentially to reduce the volume of air that comes into contact with free-falling powder and to prevent fluidization segregation. Tablets were compressed on a single-sided, 38-station rotary HATA tablet press at a target speed of 35 to 70 rpm and main compression force of approximately 0.30 metric tons.

Film-Coating:

The approximately 560 Kg of tablets is divided into five, approximately 110 Kg portions of tablets. One portion of compressed tablets was added to a 48 inch coating pan. The doxepin recipe is accessed in the process control computer and the following settings are input onto the screen.

| | |
|---|---|
| Atomization Air | 125 SLPM |
| Pattern Air | 55 SLPM |
| Nozzle Air | 72 psi |
| Gun Position | A = 8; B = 2 and C = 6 |

At the conclusion of the computer controlled application process, an average percent weight gain for the tablet cores is calculated. The above process is repeated Example 9

Comparison of SMCC with Other Direct Compression (DC) Excipients 12 kg SMCC and other common excipient formulations with colorants (Yellow #6 and Yellow #10) and doxepin at a theoretical concentration of 1 mg were generally prepared using the process set forth above.

Briefly, experiments were performed to confirm the role silicified microcrystalline cellulose (ProSolv) plays in imparting some preferred quality characteristics to low-dose doxepin tablets. Common, best-in-class, direct-compression-type excipients were directly substituted for SMCC, a high-functionality excipient, in the formulation set forth above. These substitute excipients included the following.

Vivapur (microcrystalline cellulose)
Dipac (a directly compressible sugar)
Emcompress (Dicalcium phosphate)
Mannogem (mannitol, a directly compressible alcohol)
Pharmatose (spray-dried lactose)
Starch 1500 (pre-gelatinized starch)

The compaction and ejection forces necessary to manufacture tablets from these formulations on an automated, rotary tablet press, at a target hardness value of 10 kp, were recorded. Unexpectedly, the SMCC formulation exhibited an average hardness of 9.1 kp with a standard deviation of 1.16 using a compaction force of 136 pounds. The Dipac, Pharmatose and Vivapur formulations achieved satisfactory levels of hardness but required average compaction forces of 1,204 pounds, 807 pounds, and 189 pounds, respectively.

For the SMCC and other four substitute formulations, tablets samples were systematically taken throughout the compression operation and tested for weight, hardness, thickness and friability. The SMCC formulation achieved a friability value of 0.11%. The Vivapur, Pharmatose, and the Dipac formulations achieved friability values of 0.07%, 0.09%, 0.17%, respectively.

Figure 10:
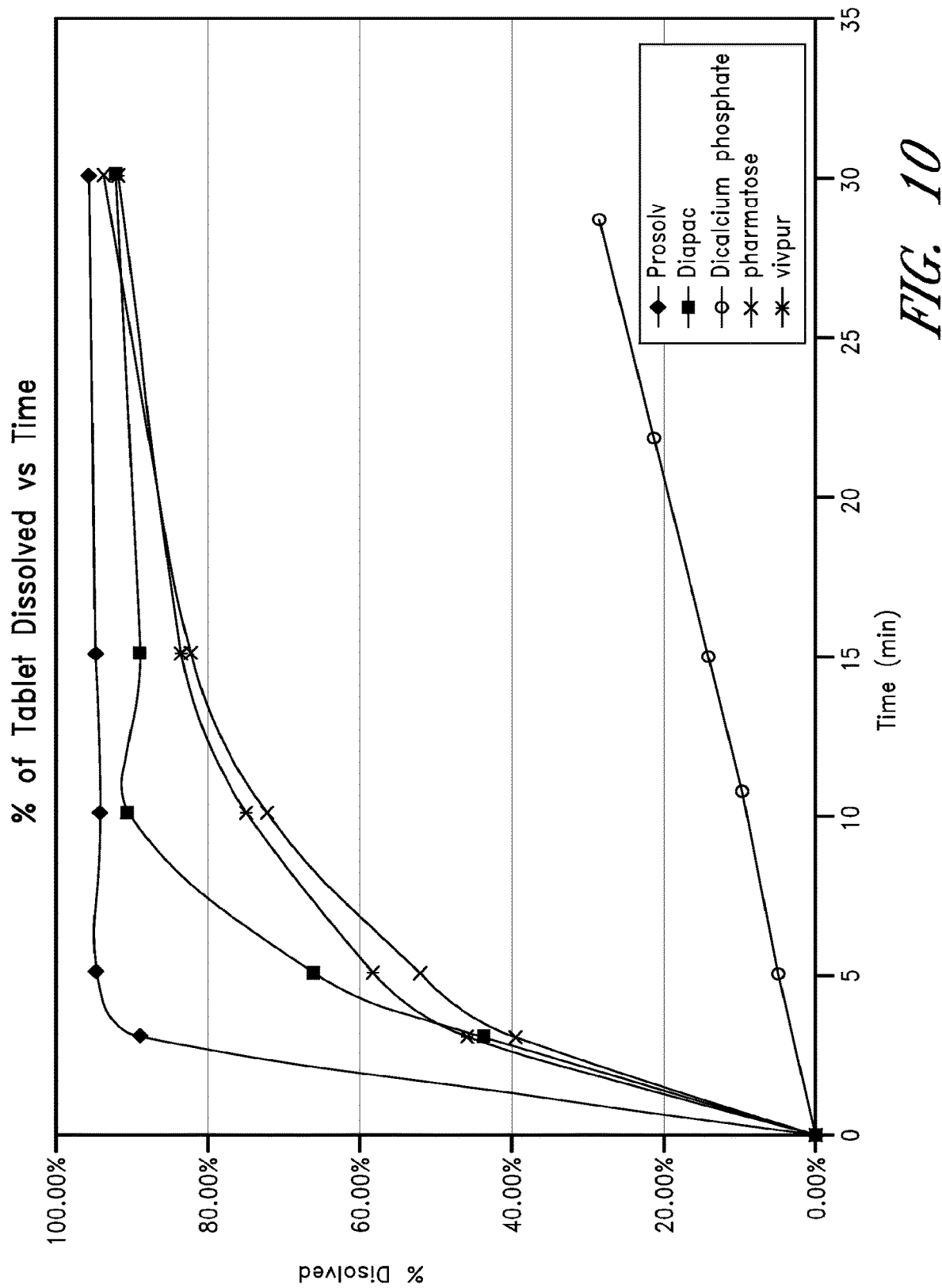
FIG. 10 is a graph showing percentage of tablet dissolved vs. time (min).

These data associated with the non-SMCC formulations were compared to the corresponding SMCC data to detect statistically significant differences in mean values (t-test) and degree of data variability (F-test). Disintegration, dissolution profile and content uniformity testing were also conducted on representative tablets samples from these compressed formulations. Dissolution profiles in simulated gastric fluid without enzyme pH 1.2 are provided in FIG. 10. Dissolution data calculations were performed to determine the $f_2$ similarity factor for each formulation relative to the SMCC formulation.

Unexpectedly, no substitute formulation achieved the threshold dissolution $f_2$ similarity factor value of 50 compared to an SMCC based formulation. The $f_2$ values ranged from 4.2 to 30.8. Disintegration is another drug product performance characteristic for which the SMCC formulation can be a preferred formulation. SMCC formulation disintegration rate was less than 6 seconds based on USP protocols. The Vivapur formulation disintegration rate was approximately 1 to 2 minutes.

The SMCC formulation statistically differentiated (i.e. p values<<0.05) itself with respect to the variability of the in-process weight data from the Vivapur formulation and in-process thickness data for substitute formulations. In addition, the SMCC formulation required lower compaction and ejection forces compared to substitute formulations. The degree of difference has significant ramifications related to tablet machine and tooling wear.

Although, SMCC demonstrates some preferred characteristics and is a preferred material in some aspects of the embodiments, it should be understood that other materials, including those tested above, can also be used alone or in combination with each other and/or SMCC in various aspects of the embodiments. Some examples of combinations are described further in the examples and elsewhere herein.

Example 10

Fluid Bed Granulation Process

Figure 11A:
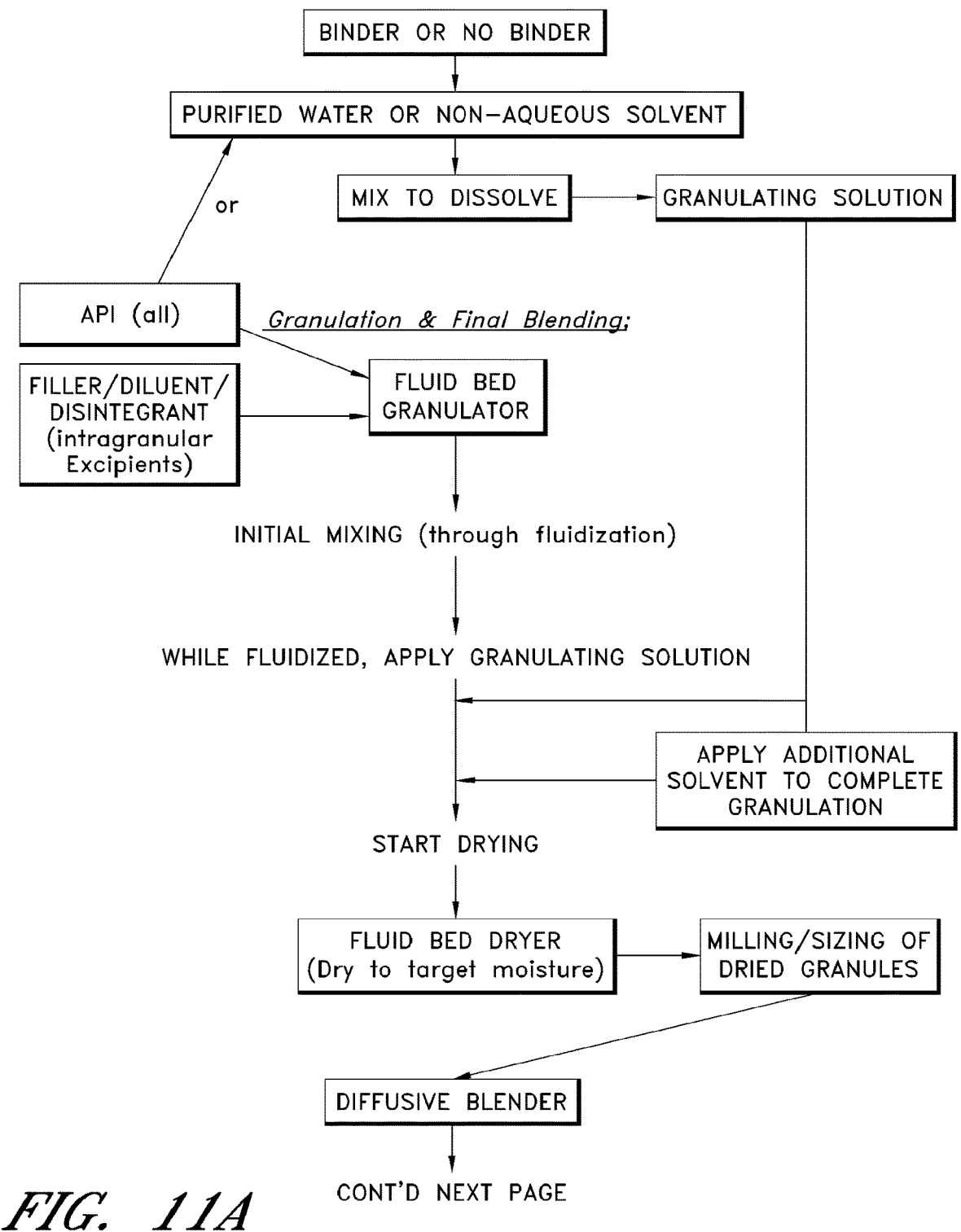
FIGS. 11A-B are flow charts showing a fluid bed granulation process for use in the invention disclosed herein.
Figure 11B:
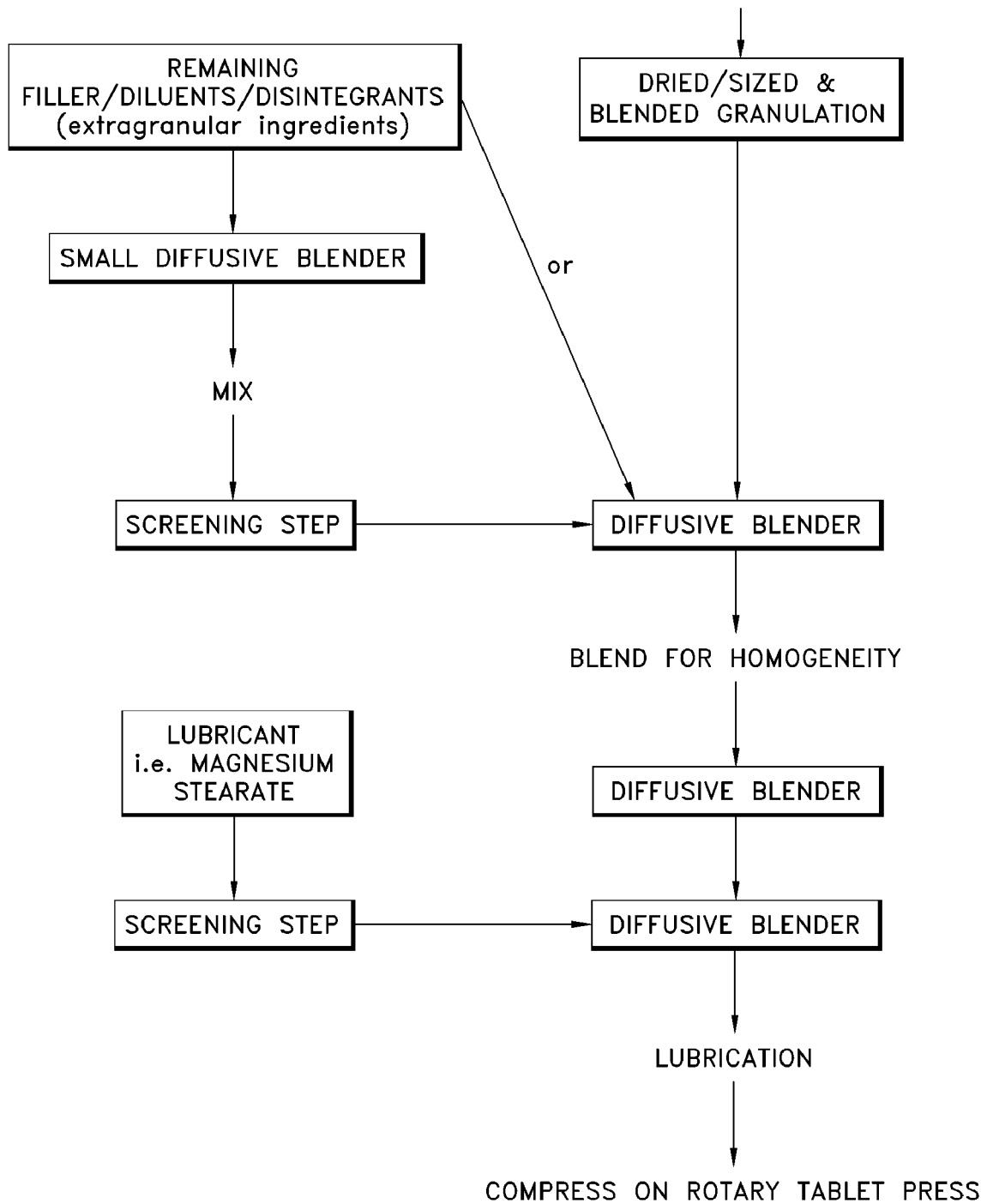

A flow chart depicting an exemplary fluid bed granulation manufacturing process for use with the formulations described herein is provided in FIGS. 11A and 11B.

Example 11

Wet Granulation Process

Figure 12A:
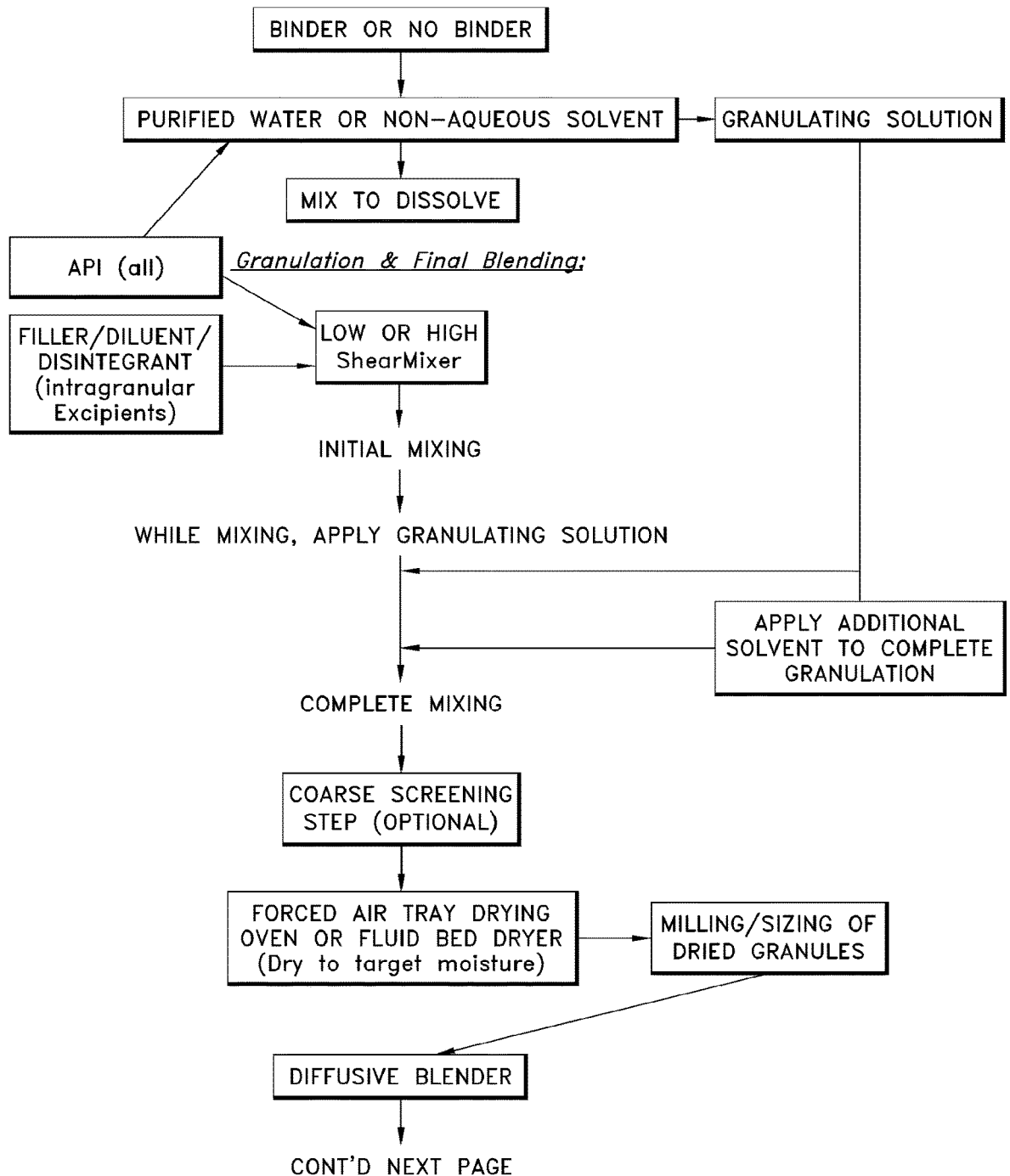
FIGS. 12A-B are flow charts showing a wet granulation process for use in the invention disclosed herein.
Figure 12B:
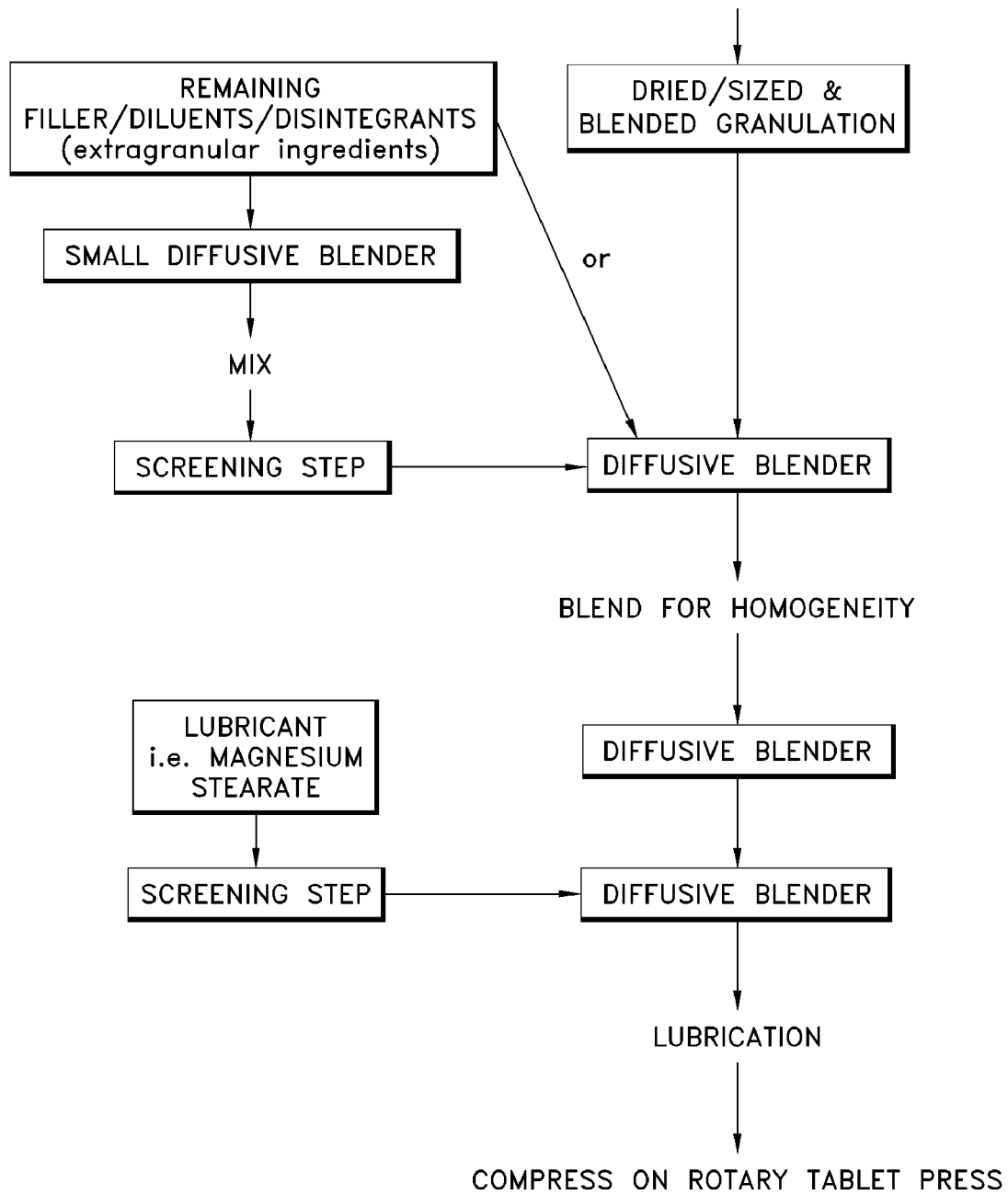

A flow chart depicting an exemplary wet granulation manufacturing process for use with the formulations described herein is provided in FIGS. 12A and 12B.

In some aspects a wet granulation process can be utilized to minimize segregation of the low dose doxepin during the production of dosage forms.

Example 12

Dry Granulation Process

Figure 13A:
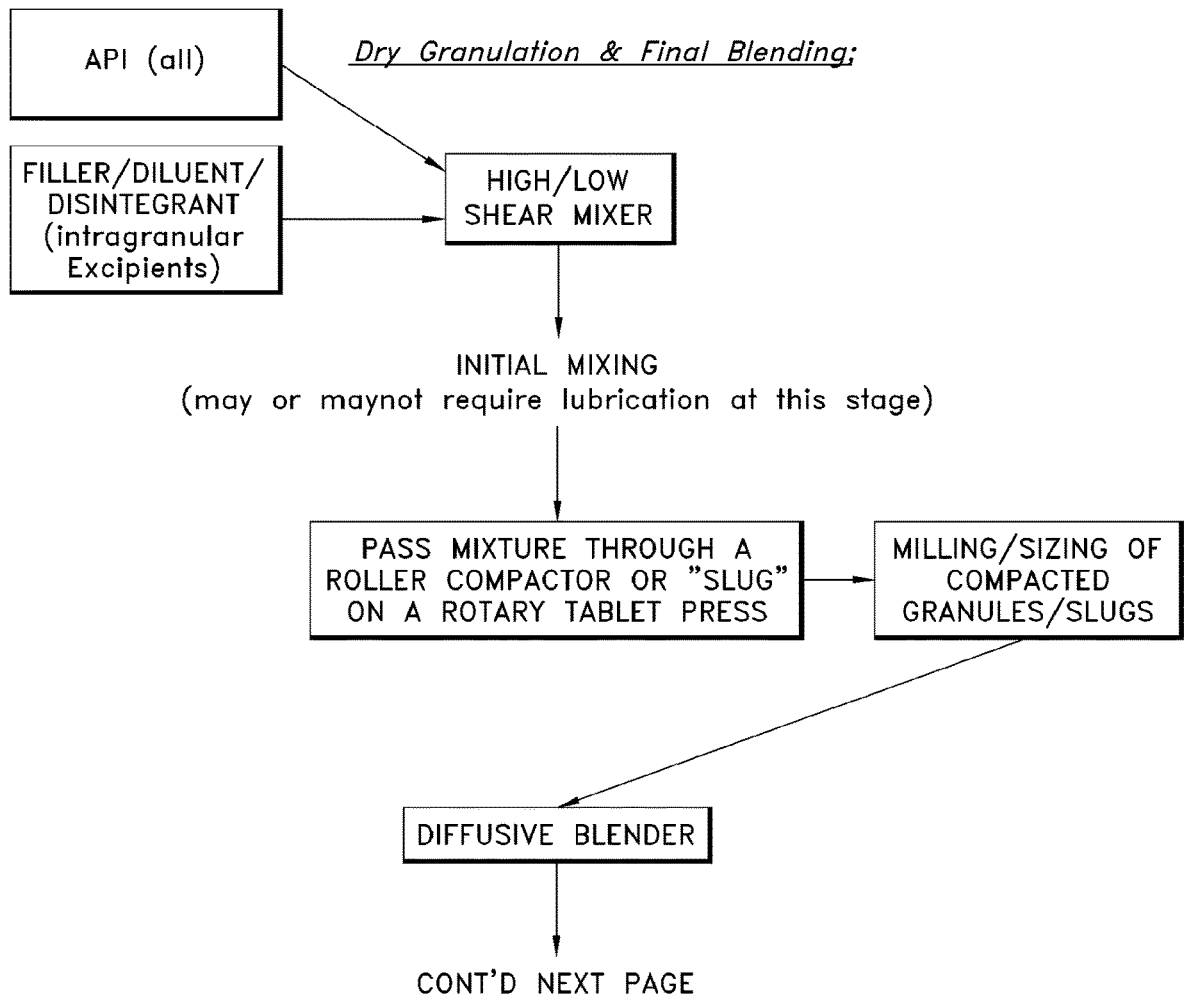
FIGS. 13A-B are flow charts showing a dry granulation process for use in the invention disclosed herein.
Figure 13B:
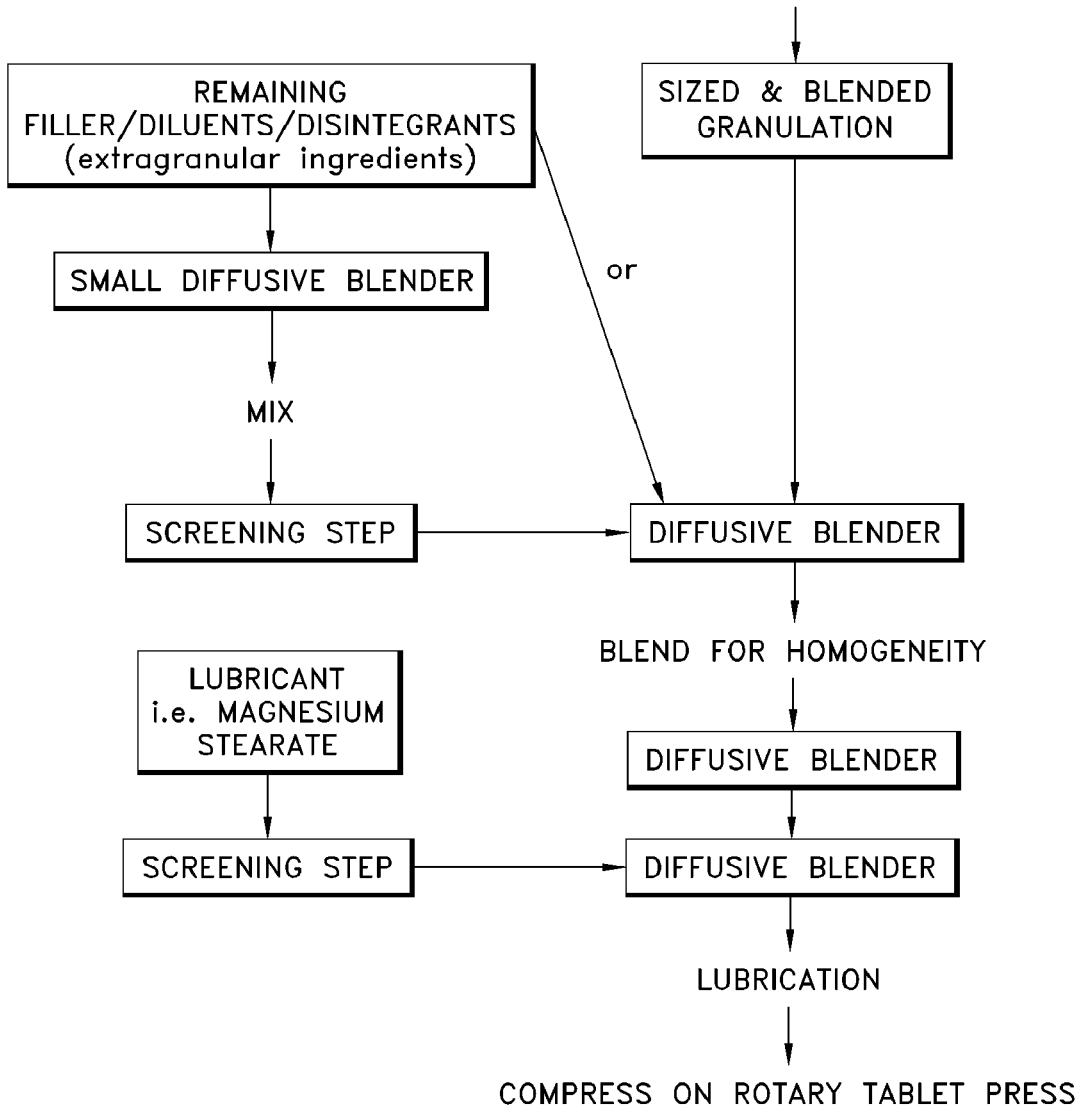

A flow chart depicting an exemplary dry granulation manufacturing process for use with the formulations described herein is provided in FIGS. 13A and 13B.

Example 13

Formulations Demonstrating Unique pK Profile

The pharmacokinetic performance of oral, low dose doxepin formulations is well suited to the treatment of insomnia. The pharmacokinetic performance of capsules containing 1, 3 or 6 mg doxepin, as well as tablets containing 6 mg doxepin, was evaluated in healthy adult volunteers under a crossover design.

Table 5 presents the results.

TABLE 5

| Descriptive Statistics for Doxepin Pharmacokinetic Parameters | | | | |
|---|---|---|---|---|
| Parameter (Unit)[a] | (6 mg capsules) | (6 mg tablets) | (3 mg capsule) | (1 mg capsules) |
| $AUC_{0-t}$ (ng*h/mL) | 13.76 (82.9) [n = 16] | 13.03 (70.8) [n = 16] | 5.689 (68.9) [n = 13] | 1.561 (76.7) [n = 13] |
| $AUC_{0-\infty}$ (ng*h/mL) | 16.26 (81.6) [n = 16] | 15.19 (69.1) [n = 16] | 7.518 (64.6) [n = 12] | [b] [n = 2] |
| $C_{max}$ (ng/mL) | 0.9458 (64.5) [n = 16] | 0.8864 (59.4) [n = 16] | 0.4445 (54.0) [n = 13] | 0.1587 (55.5) [n = 15] |
| $T_{max}$ (h) | 4.0 (1.0-6.0) [n = 16] | 3.5 (2.0-6.0) [n = 16] | 4.0 (1.0-6.0) [n = 13] | 4.0 (1.5-8.0) [n = 14] |
| $t_{1/2}$ (h) | 15.13 (41.9) [n = 16] | 15.32 (31.3) [n = 16] | 14.28 (46.8) [n = 12] | [b] [n = 5] |

[a] Estimates presented are the arithmetic mean and (CV%) for AUC, $C_{max}$ and $t_{1/2}$ and the median and (range) for $T_{max}$.
[b] Parameter could not be calculated accurately.

Of special note was the time taken to reach the maximum plasma concentration (Tmax), which, on average, was 3.5-4 hours for all doses, and the half-life, which, on average, fell between 14.28 and 15.32 hours. Of further interest to the pharmacokinetic performance of these doxepin formulations was the time necessary to reach certain plasma concentrations. Reaching particular concentrations in plasma can play a role in establishing therapeutic benefit. In particular, doxepin concentrations in plasma reach 0.05 ng/mL in the majority of subjects for all doses within 90 minutes after dosing. For the 3 and 6 mg doses, a plasma concentration of 0.1 ng/mL was reached in the majority of subjects within 60 minutes of dosing. Such pharmacokinetic performance is beneficial in the treatment of insomnia, as reaching measurable plasma concentrations in a timely manner can be preferred for facilitating the onset of sleep.

Thus, the therapeutic properties of doxepin in insomnia are reflected in a correspondence between plasma concentrations and the state of wakefulness, as well as the particular profile of such concentrations over the course of the night. Taking the 3 mg dose as an example, doxepin plasma concentrations, on average, reached 0.1 mg/mL approximately 1 hour after dosing. Because of doxepin's high affinity for histamine H1 receptors, this concentration is sufficient to initiate and maintain sleep. Accordingly, taking the customary pretreatment period of 30 minutes before bed into account, sleep onset can occur approximately at the time the concentration reached 0.1 ng/mL. This preferable concentration may vary due to individual differences in drug sensitivity or disease severity. In examining polysomnographic endpoints in adult insomnia patients treated with 3 mg doxepin, sleep onset was reached, on average, 27 minutes after bedtime, a time point roughly 1 hour after dosing. Further, the same patients experienced improvements in the maintenance of sleep. In accordance with the pharmacokinetic profile afforded by doxepin formulations, the improvements in sleep maintenance persisted throughout the entire night (8 hours) but not followed by residual sedation. The combination of high solubility and high permeability with rapid dissolution, absorption and a metabolic clearance rate which afforded therapeutic concentrations throughout the night all contributed to the beneficial pharmacokinetic profile. Having a formulation with a rapid absorption phase corresponding with Cmax at 3-4 hours post-dose, and a half-life of approximately 14-15 hours can be preferable for the safety and efficacy profile of low dose doxepin in insomnia.

Thus, some embodiments relate to formulations comprising low dose doxepin, preferably between about 0.5 and 7 mg doxepin, which formulations after administration (e.g., to a 70 kg human), provide a plasma concentration of at least 0.05 ng/mL doxepin within a time frame of not more than about 80 or 90 minutes or a plasma concentration of at least 0.1 ng/mL within a time frame of not more than about 50 or 60 minutes.

The formulations of some of the present embodiments can provide rapid rise in plasma concentrations following administration, e.g., achieving a plasma concentration of about 0.1 ng/mL following a 3 mg or a 6 mg dose in 60 minutes or less, for example, within 50 minutes, 45 minutes, 40 minutes, 35 minutes, 30 minutes, or less. Also, some can achieve plasma concentrations of about 0.05 ng/mL following a 1 mg, 3 mg or a 6 mg dose in 90 minutes or less, for example, 85 minutes or less, 80 minutes or less, 75 minutes or less, 70 minutes or less, 65 minutes or less, 60 minutes or less, for example, within 50 minutes, 45 minutes, 40 minutes, 35 minutes, 30 minutes, or less. Accordingly, some embodiments relate to formulations and dosage forms that result in more rapid achievement of effective plasma concentrations of doxepin leading to more rapid drug onset (e.g., sleep onset) at the dosages described herein, including, for example, dosages of 1 mg, 3 mg or 6 mg.

Furthermore some embodiments relate to formulations comprising low dose doxepin, which formulations after administration result in any one or more of the pK results shown in Table 5. For example, the formulations can result in an AUC from about 1.4 to about 14 ng*h/mL. Preferably, a 1 mg formulation upon administration can result in an AUC of about 1.5 ng*h/mL. Preferably, a 3 mg formulation upon administration can result in an AUC of about 5-6 ng*h/mL. Preferably, a 6 mg formulation upon administration can result in an AUC of about 12.5-14 ng*h/mL.

Some embodiments relate to formulations that upon administration can result in a $C_{max}$ of about 0.15 ng/mL to about 1.0 ng/mL. Preferably, a 1 mg formulation upon administration can result in a $C_{max}$ of about 0.14-0.16 ng/mL. Preferably, a 3 mg formulation upon administration can result in a $C_{max}$ of about 0.4-0.5 ng/mL. Also, preferably, a 6 mg formulation upon administration can result in a $C_{max}$ of about 0.8-1.0 ng/mL.

Example 14

Alternate Formulations

In some embodiments, SMCC is combined or replaced with one or more of the following excipients: microcrystalline cellulose, lactose monohydrate (spray dried), a compressible sugar, xylitol (Xylitab), sorbitol, mannitol, pregelatinized starch, maltodextrin, calcium phosphate dibasic, calcium phosphate tribasic, calcium carbonate DC, and the like. Accordingly, in one embodiment, assuming the total filler to be 100%, about 50% SMCC is combined with about 50% microcrystalline cellulose, lactose monohydrate (spray dried), a compressible sugar, xylitol (Xylitab), sorbitol, mannitol, pregelatinized starch, maltodextrin, calcium phosphate dibasic, calcium phosphate tribasic, calcium carbonate DC, or a combination of any of the same.

In alternate embodiments, SMCC is entirely replaced with one or more alternate excipients. For example, in one embodiment a 50:50 ratio of microcrystalline cellulose to lactose is used in place of SMCC. In this example, the overall compressibility of the lactose is improved allowing for less compression force resulting in a more porous tablet or caplet that shows improved dissolution over the microcrystalline cellulose or lactose alone.

In some embodiments, the formulation includes at least one additional pharmaceutically acceptable excipient, such as a binder, a diluent, a disintegrant, a lubricant, a filler, a carrier, and the like, to improve, for example, the direct compression tablet-forming properties of the dry blend, and/or powder flowability. When incorporated into the formulations disclosed herein, the amounts of the major filler(s) can be reduced accordingly to accommodate the amount of additional excipient(s) added in order to keep the overall unit weight of the tablet unchanged.

For example, in some embodiments, colloidal silicon dioxide, is added to the formulation as a glidant to facilitate mass flow of the powder mixture during blending and tablet compression operations. Colloidal silicon dioxide is added at concentrations ranging from about 0.1% to about 5.0% w/w, or from about 0.25% to about 2% w/w, or from about 0.5% to about 1% w/w.

In some embodiments, magnesium stearate is added as a lubricant to improve powder flow, prevent the blend from adhering to tableting equipment and punch surfaces and provide lubrication to allow tablets to be cleanly ejected from tablet dies. Magnesium stearate is added to pharmaceutical formulations at concentrations ranging from about 0.1% to about 5.0% w/w, or from about 0.25% to about 2% w/w, or from about 0.5% to about 1% w/w.

In some embodiments, at least one binder is added to enhance the compressibility of the major excipient(s). In some embodiments, the formulation includes at least one of the following binders in the following preferred ranges: from about 2 to about 6% w/w hydroxypropyl cellulose (Klucel), from about 2 to about 5% w/w polyvinylpyrrolidone (PVP), from about 1 to about 5% w/w methylcellulose, from about 2 to about 5% hydroxypropyl methylcellulose, from about 1 to about 5% w/w ethylcellulose, from about 1 to about 5% w/w sodium carboxy methylcellulose, and the like.

In some embodiments, the formulations include at least one lubricant in the following preferred ranges: from about 0.25 to about 2% w/w magnesium stearate, from about 0.25 to about 2% w/w calcium stearate, from about 0.25 to about 2% w/w sodium stearyl fumarate, from about 0.25 to about 2% w/w stearic acid, from about 0.25 to about 2% w/w hydrogenated vegetable oil, from about 0.25 to about 2% w/w glyceryl behenate, from about 0.25 to about 2% w/w polyethylene glycol 4000-6000, and the like.

In some embodiments, at least one additional disintegrant is included to facilitate tablet disintegration after administration. For example, at least one of the following preferred disintegrants is added in the following preferred ranges: from about 1 to about 3% w/w croscarmellose sodium, from about 4 to about 6% w/w sodium starch glycolate, from about 2 to about 4% w/w crospovidone, from about 10 to about 20% w/w microcrystalline cellulose, from about 5 to about 10% w/w pregelatinized starch, from about 5 to about 10% w/w corn starch, from about 5 to about 10% w/w alginic acid, from about 1 to about 5% w/w ion exchange resin (Amberlite 88), and the like.

The alternate formulations described above provide favorable drug processing qualities, including, for example, rapid tablet press speeds, reduced compression force, reduced ejection force, blend uniformity, content uniformity, uniform dispersal of color, accelerated disintegration time, rapid dissolution, low friability, and the like. For example, the formulations achieve average hardness values of at least 2 Kp using minimal compaction force, average friability values of 1% or less, and disintegration rates of 1 minute or less based on USP protocols. In addition, the alternate formulations each result in a batch of dosage forms having content uniformity values between 85% to 115% of label claim with a relative standard deviation of 6% or less.

It should be noted that some embodiments can specifically exclude the formulations that include one or more of the following ingredients used with doxepin. In some aspects, the methods and formulation can specifically exclude formulations that include the following hard gelatin capsules (which may contain Blue 1, Red 3, Red 40, Yellow 10, and other inert ingredients); magnesium stearate; sodium lauryl sulfate; starch; glycerin; methylparaben; peppermint oil; propylparaben; water and 10 mg of doxepin or more.

Many modifications and variations of the embodiments described herein may be made without departing from the scope, as is apparent to those skilled in the art. The specific embodiments described herein are offered by way of example only.

We claim:

1. A method of treating insomnia, the method comprises administering to a patient in need thereof a pharmaceutical composition comprising about 0.5 to about 7 mg of doxepin, or a pharmaceutically acceptable salt thereof, and about 80% to about 99.8% w/w silicified microcrystalline cellulose.

2. The method of claim 1, wherein administering the composition provides a plasma concentration of at least 0.05 ng/mL doxepin within a time frame of not more than about 90 minutes.

3. The method of claim 1, wherein the composition further comprises about 0.1 to about 1.5% w/w colloidal silicon dioxide.

4. The method of claim 1, wherein the composition further comprises about 0.25 to about 1.5% w/w magnesium stearate.

5. The method of claim 1, wherein the composition comprises about 0.8 to about 2 mg of doxepin or a pharmaceutically acceptable salt thereof.

6. The method of claim 1, wherein the composition comprises about 2.5 to about 4 mg of doxepin or a pharmaceutically acceptable salt thereof.

7. The method of claim 1, wherein the composition comprises about 3 mg of doxepin or a pharmaceutically acceptable salt thereof.

8. The method of claim 1, wherein the composition comprises about 5.5 to about 7 mg of doxepin or a pharmaceutically acceptable salt thereof.

9. The method of claim 1, wherein the composition comprises about 6 mg of doxepin or a pharmaceutically acceptable salt thereof.

10. The method of claim 1, wherein the composition further comprises one or more of colloidal silicon dioxide or magnesium stearate.

11. The method of claim 1, wherein the insomnia is a chronic insomnia.

12. The method of claim 1, wherein the insomnia is a non-chronic insomnia.

13. The method of claim 1, wherein the insomnia is a non-chronic insomnia.

14. The method of claim 1, wherein the patient suffers from difficulties in sleep onset.

15. The method of claim 1, wherein the patient suffers from difficulties in sleep maintenance.

16. The method of claim 1, wherein the patient suffers from difficulties in sleep duration.

17. The method of claim 1, wherein the patient suffers from difficulties in sleep efficiency.

18. The method of claim 1, wherein the patient suffers from difficulties in premature early-morning awakening.

19. The method of claim 1, wherein the composition comprises a tablet.

20. The method of claim 1, wherein administering the composition provides a plasma concentration of at least 0.1 ng/mL doxepin within a time frame of not more than about 60 minutes.

* * * * *